United States Patent [19]
de Laszlo et al.

[11] Patent Number: 5,202,328
[45] Date of Patent: Apr. 13, 1993

[54] SUBSTITUTED FUSED PYRIMIDINONES

[75] Inventors: Stephen E. de Laszlo, Atlantic Highlands; Eric E. Allen, Edison; William J. Greenlee, Teaneck; Arthur A. Patchett, Westfield, all of N.J.

[73] Assignee: Merck & Co., Inc., Rahway, N.J.

[21] Appl. No.: 665,517

[22] Filed: Mar. 6, 1991

[51] Int. Cl.$^5$ .................. A61K 31/505; A61K 31/52; C07D 487/00; C07D 473/00
[52] U.S. Cl. ..................................... 514/258; 514/262; 544/255; 544/262; 544/265; 544/278; 544/280
[58] Field of Search ............... 544/265, 262, 255, 278, 544/280; 514/262, 258

[56] References Cited

U.S. PATENT DOCUMENTS
4,870,186  9/1989  Aldrich et al. ............... 548/215
4,880,804  11/1989  Carini et al. ............... 514/234.5

FOREIGN PATENT DOCUMENTS
58696     7/1990   Australia .
0253310   1/1988   European Pat. Off. .
0399731   5/1990   European Pat. Off. ........... 471/4
412848    8/1990   European Pat. Off. .
407342    1/1991   European Pat. Off. .
8908113   9/1989   World Int. Prop. O. .

OTHER PUBLICATIONS

Chin et al., European Journal of Pharmacology, 157(1988) 13–21.
Piper et al., J. Med. Chem. (1980) 23(10) 1136–1139.
P. C. Wong et al., European J. Pharma., 202, p. 323 (1991).
Ziegler et al., J. Org. Che. 43(5) (1978).

Primary Examiner—Mukund J. Shah
Assistant Examiner—Matthew V. Grumbling
Attorney, Agent, or Firm—William H. Nicholson; Joseph F. DiPrima

[57] ABSTRACT

Novel substituted fused pyrimidinones of formula (I), which are useful as angiotensin II antagonists, are disclosed.

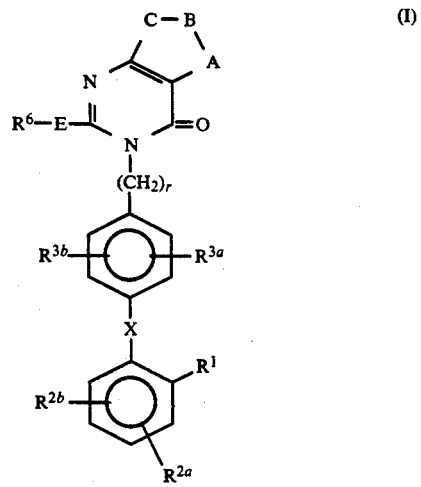

7 Claims, No Drawings

SUBSTITUTED FUSED PYRIMIDINONES

INTRODUCTION OF THE INVENTION

This invention relates to novel substituted fused pyrimidinone compounds which are useful as angiotensin II antagonists in the treatment of elevated blood pressure and congestive heart failure. Thus, the substituted fused pyrimidinone compounds of the invention are useful as antihypertensives.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 323,841; and 324,377; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988), *Hypertension*, 13, 489–497 (1989)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted fused pyrimidinone compounds which are useful as angiotensin II antagonists, as antihypertensives, in the treatment of congestive heart failure, and in the treatment of elevated intraocular pressure. The compounds of this invention have the general formula (I):

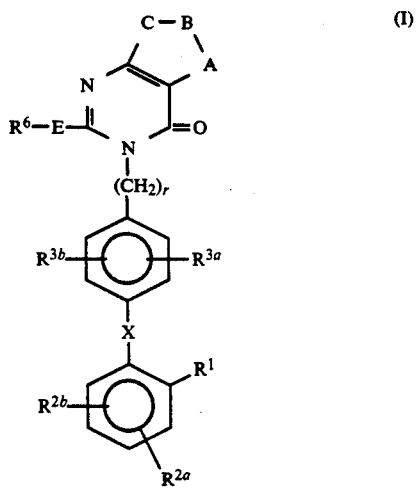

wherein:

A-B-C together with the pyrimidinone to which it is attached form a member selected from the group:

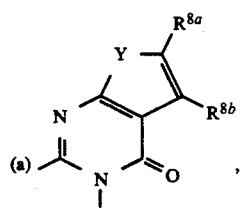

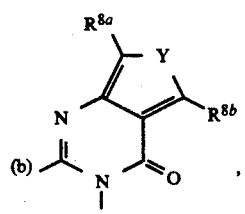

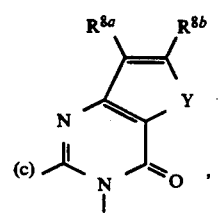

3

-continued

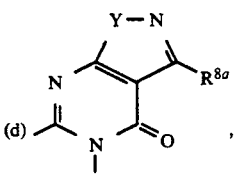

(d)

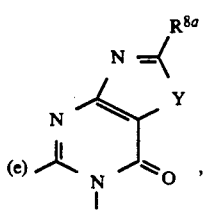

(e)

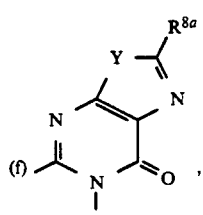

(f)

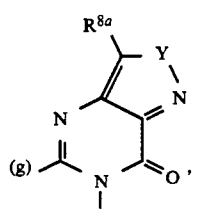

(g)

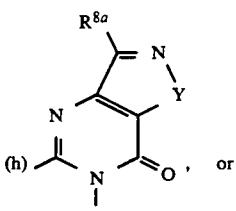

(h) , or

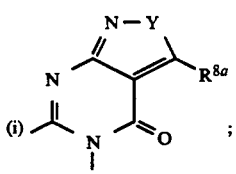

(i) ;

Y is O, S or $NR^7$;
$R^1$ is
(a) $-CO_2R^4$,
(b) $-SO_3R^5$,
(c) $-NHSO_2R^{22}$,
(d) $-PO(OR^5)_2$,
(e) $-SO_2-NH-R^{22}$,

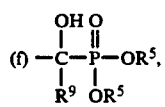

(f) ,

4

-continued

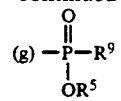

(g)

(h) $-CH_2SO_2NH-R^{22}$,
(i) $-SO_2NH-CO-R^{22}$,
(j) $-CH_2SO_2NH-CO-R^{22}$,
(k) $-CONH-SO_2R^{22}$,
(l) $-CH_2CONH-SO_2R^{22}$,
(m) $-NHSO_2NHCO-R^{22}$,
(n) $-NHCONHSO_2-R^{22}$,

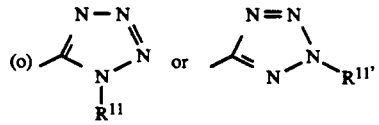

(o) or

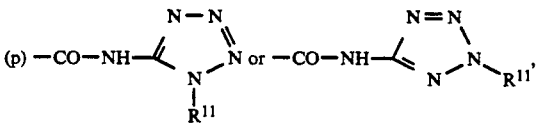

(p) $-CO-NH-$ or $-CO-NH-$ (q) $-CONHNHOS_2CF_3$,
(r) $-SO_2NH-CN$,

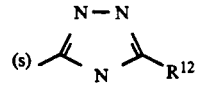

(s)

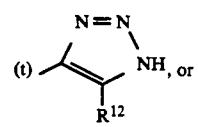

(t) , or (u) $-SO_2NHCONR^4R^{22}$,
wherein
n is 1 to 3, Z is O, S or $NR^4$, heteroaryl is an unsubstituted, monosubstituted or disubstituted five or six membered aromatic ring which contains from 1 to 3 heteroatoms selected from the group consisting of O, N or S and wherein the substituents are members selected from the group consisting of $-OH$, $-SH$, $-C_1-C_4$-alkyl, $-C_1-C_4$-alkoxy, $-CF_3$, Cl, Br, F, I, $-NO_2$, $-CO_2H$, $-CO_2-(C_1-C_4$-alkyl), $-NH_2$, $-NH(C_1-C_4$-alkyl) and $-N(C_1-C_4$-alkyl)$_2$;
$R^{2a}$ and $R^{2b}$ are each independently
(a) H,
(b) Cl, Br, I, or F,
(c) $NO_2$,
(d) $NH_2$,
(e) $C_1-C_4$-alkylamino,
(f) di($C_1-C_4$-alkyl)amino,
(g) $SO_2NHR^9$,
(h) $CF_3$,
(i) $C_1-C_6$-alkyl,
(j) $C_1-C_6$-alkoxy,
(k) $C_1-C_6$-alkyl-S—,
(l) $C_2-C_6$-alkenyl,
(m) $C_2-C_6$-alkynyl,
(n) aryl,
(o) aryl($C_1-C_4$-alkyl), or (p) C₃-C₇-cycloalkyl;

R³ᵃ is
(a) H,
(b) Cl, Br, I, or F,
(c) C₁-C₆-alkyl,
(d) C₁-C₆-alkoxy, or
(e) C₁-C₆-alkoxyalkyl;

R³ᵇ is
(a) H,
(b) Cl, Br, I, or F,
(c) NO₂,
(d) C₁-C₆-alkyl,
(e) C₁-C₆-acyloxy,
(f) C₃-C₇-cycloalkyl,
(g) C₁-C₆-alkoxy,
(h) —NHSO₂R⁴,
(i) hydroxy(C₁-C₄-alkyl),
(j) aryl(C₁-C₄-alkyl),
(k) C₁-C₄-alkylthio,
(l) C₁-C₄-alkyl sulfinyl,
(m) C₁-C₄-alkyl sulfonyl,
(n) NH₂,
(o) C₁-C₄-alkylamino,
(p) di(C₁-C₄-alkyl)amino,
(q) fluoro-C₁-C₄-alkyl-,
(r) —SO₂—NHR⁹,
(s) aryl,
(t) furyl,
(u) CF₃,
(v) C₂-C₆-alkenyl, or
(w) C₂-C₆-alkynyl;

wherein
aryl is phenyl or naphthyl or substituted phenyl or naphthyl with one or two substituents selected from the group consisting of Cl, Br, I, F, N(R⁴)₂, CO₂R⁴, C₁-C₄-alkyl, C₁-C₄-alkoxy, NO₂, CF₃, C₁-C₄-alkylthio, OH, or —SO(C₁-C₄-alkyl);

R⁴ is H, aryl, C₁-C₆ alkyl, or substituted C₁-C₆ alkyl with an aryl or heteroaryl substituent;

R⁴ᵃ is aryl, C₁-C₆ alkyl, or substituted C₁-C₆ alkyl with an aryl substituent;

R⁵ is H,

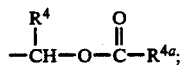

E is a single bond, —NR¹³(CH₂)ₛ—, —S(O)ₓ(CH₂)ₛ— where x is 0 to 2 and s is 0 to 5, —CH(OH)—, —O—, CO—;

R⁶ is
(a) aryl or substituted aryl with 1 or 2 substituents selected from the group consisting of Cl, Br, I, F, —O—C₁-C₄-alkyl, C₁-C₄-alkyl, —NO₂, —CF₃, —SO₂NR⁹R¹⁰, —S—C₁-C₄-alkyl, —OH, —NH₂, C₃-C₇-cycloalkyl, C₃-C₁₀-alkenyl,
(b) C₁-C₆-alkyl, C₂-C₅-alkenyl or C₂-C₅-alkynyl or substituted C₁-C₆-alkyl, C₂-C₅-alkenyl or C₂-C₅-alkynyl substituted with a substituent selected from the group consisting of aryl, C₃-C₇-cycloalkyl, Cl, Br, I, F, CF₃, CF₂CF₃, —NH₂, —NH(C₁-C₄-alkyl), —OR⁴ —N(C₁-C₄-alkyl)₂, —NH—SO₂R⁴, —COOR⁴, —SO₂NHR⁹,
(c) an unsubstituted, monosubstituted or disubstituted heteroaromatic 5 to 6 membered cyclic ring which contains one to three members selected from the group consisting of N, O, S, and wherein the substitutents are members selected from the group consisting of —OH, —SH, C₁-C₄-alkyl, C₁-C₄-alkoxy, —CF₃, Cl, Br, I, F, or NO₂,
(d) C₃-C₇-cycloalkyl,
(e) perfluoro-C₁-C₄-alkyl, or
(f) H;

R⁷ is:
(a) H,
(b) C₁-C₆-alkyl, C₂-C₆-alkenyl or C₂-C₆-alkynyl or substituted C₁-C₆-alkyl, C₂-C₆-alkenyl or C₂-C₆-alkynyl substituted with a substituent selected from the group consisting of C₃-C₇-cycloalkyl, Cl, Br, I, F, —OH, —NH₂, —NH(C₁-C₄-alkyl), —N(C₁-C₄ alkyl)₂, —NHSO₂R⁴, —COOR⁴, C₁-C₄-alkoxyl, C₁-C₄-alkylthio, —CONH₂, —COR⁴, —SO₂R⁴, —NR⁴COR²², —NR⁴CO₂R²², —NR⁴CONR⁴R²² or —CO heteroaryl,
(c) —COR⁴,
(d) aryl, or substituted aryl wherein the substitutents are V or W.
(e) aryl-C₁-C₆-alkyl in which the aryl group is unsubstituted, mono- or disubstituted with V or W,
(f) —OR⁴,
(g) heteroaryl, or
(h) —CON(R⁴)₂;

V and W are independently:
(a) H,
(b) C₁-C₅-alkoxy,
(c) C₁-C₅-alkyl,
(d) hydroxy,
(e) C₁-C₅-alkyl-S(O)ₓ—,
(f) CN,
(g) NO₂,
(h) N(R⁴)₂,
(i) CON(R⁴)₂,
(j) CO₂R⁴,
(k) COR⁴,
(l) CF₃,
(m) Cl, Br, I, or F,
(n) hydroxy-C₁-C₅-alkyl,
(o) C₁-C₅-alkylthio,
(p) —SO₂NR⁹R¹⁰,
(q) C₃-C₇-cycloalkyl, or
(r) C₂-C₁₀-alkenyl;

R⁸ᵃ and R⁸ᵇ are independently
(a) H,
(b) C₁-C₈-alkyl, C₂-C₆-alkenyl or C₂-C₆-alkynyl or substituted C₁-C₈-alkyl, C₂-C₆-alkenyl or C₂-C₆-alkynyl with a substituent selected from the group consisting of —OH, -guanidino, C₁-C₄-alkoxy, —N(R⁴)₂, COOR⁴, —CON(R⁴)₂, —O—COR⁴, -aryl, -heteroaryl, —S(O)ₓ—R²², -tetrazol-5-yl, —CONHSO₂R²², —SO₂NH-heteroaryl, —SO₂NHCOR²², —PO(OR⁴)₂, —PO(OR⁴)R⁹, —SO₂NH-CN, —NR¹⁰COOR²², —(CH₂)₁₋₄R⁴, Cl, Br, F, or I,
(c) —CO-aryl,
(d) —C₃-C₇-cycloalkyl,
(e) Cl, Br, I, or F,
(f) —OH,
(g) —OR²²,
(h) —C₁-C₄-perfluoroalkyl,
(i) —S(O)ₓ—R²²,
(j) —COOR⁴,
(k) —SO₃H,
(l) —NR²²ᵃR²²,
(m) —NR²²ᵃCOR²²,
(n) —NR²²ᵃCOOR²²,
(o) —SO₂NR⁴R⁹, (p) —$NO_2$,
(q) —$N(R^{22a})SO_2R^{22}$,
(r) —$NR^{22a}CONR^4R^{22}$,

(s) —$OCNR^{22}R^9$, (t) -aryl or -heteroaryl,
(u) —$SO_2NH$-heteroaryl,
(v) —$SO_2NHCOR^{22}$,
(w) —$CONHSO_2R^{22}$,
(x) —$PO(OR^4)_2$,
(y) —$PO(OR^4)R^4$,
(z) -tetrazol-5-yl,
(aa) —$CONH$(tetrazol-5-yl),
(bb) —$COR^4$,
(cc) —$SO_2NHCN$,
(dd) —$NR^4SO_2NR^4R^{22}$,
(ee) —$NR^4SO_2OR^{22}$,
(ff) —$CONR^4R^{22}$,

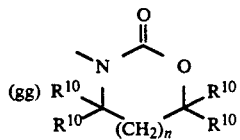
(gg)

where n=0 or 1, or

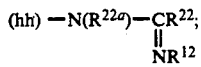
(hh)

$R^9$ is H, $C_1$-$C_5$-alkyl, aryl or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxy alkyl, or

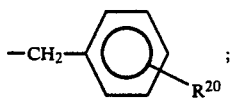

$R^{12}$ is —CN, —$NO_2$, —$CF_3$ or —$CO_2R^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;
$R^{17}$ is —$NR^9R^{10}$, —$OR^{10}$, —$NHCONH_2$, —$NHCSNH_2$,

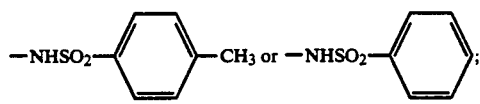

$R^{18}$ and $R^{19}$ are independently $C_1$-$C_4$-alkyl or taken together are —$(CH_2)_q$— where q is 2 or 3;
$R^{20}$ is H, —$NO_2$, —$NH_2$, —OH or —$OCH_3$;
$R^{21}$ is
(a) aryl,
(b) heteroaryl, or
(c) $C_1$-$C_4$-alkyl or substituted $C_1$-$C_4$-alkyl with a substituent selected from the group consisting of aryl, heteroaryl, —OH, —$NH_2$, —$NH(C_1$-$C_4$-alkyl), —$N(C_1$-$C_4$-alkyl)$_2$, —$CO_2R^{4a}$, Cl, Br, F, I, or —$CF_3$;

$R^{22}$ is
(a) aryl,
(b) heteroaryl,
(c) $C_3$-$C_7$-cycloalkyl,
(d) $C_1$-$C_6$-alkyl or substituted $C_1$-$C_6$-alkyl with a substituent selected from the group consisting of aryl, heteroaryl, —OH, —SH, $C_1$-$C_4$-alkyl, —$O(C_1$-$C_4$-alkyl), —$S(C_1$-$C_4$-alkyl), —$CF_3$, Cl, Br, F, I, —$NO_2$, —$CO_2H$, $CO_2$—($C_1$-$C_4$-alkyl), —$NH_2$, —$NH(C_1$-$C_4$-alkyl), —$N(C_1$-$C_4$-alkyl)$_2$, —$PO_3H_2$, —$PO(OH)(O$—$C_1$-$C_4$-alkyl), —$PO(OR^4)R^9$, morpholinyl or N—($C_1$-$C_4$ alkyl)-piperazinyl, or
(e) perfluoro-$C_1$-$C_4$-alkyl;

$R^{22a}$ is
(a) hydrogen,
(b) aryl,
(c) heteroaryl,
(d) $C_3$-$C_7$-cycloalkyl,
(e) $C_1$-$C_6$-alkyl or substituted $C_1$-$C_6$-alkyl with a substituent selected from the group consisting of aryl, heteroaryl, —OH, —SH, $C_1$-$C_4$-alkyl, —$O(C_1$-$C_4$-alkyl), —$S(C_1$-$C_4$-alkyl), —$CF_3$, Cl, Br, F, I, —$NO_2$, —$CO_2H$, $CO_2$—($C_1$-$C_4$-alkyl), —$NH_2$, —$NH(C_1$-$C_4$-alkyl), —$N(C_1$-$C_4$-alkyl)$_2$, —$PO_3H_2$, —$PO(OH)(O$—$C_1$-$C_4$-alkyl), —$PO(OR^4)R^9$, morpholinyl or N—($C_1$-$C_4$-alkyl)-piperazinyl, or
(f) perfluoro-$C_1$-$C_4$-alkyl;

X is
(a) a carbon-carbon single bond,
(b) —CO—,
(c) —O—,
(d) —S—,

(e)

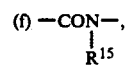
(f)

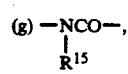
(g)

(h) —$OCH_2$—,
(i) —$CH_2O$—
(j) —$SCH_2$—,
(k) —$CH_2S$—,
(l) —$NHC(R^9)(R^{10})$,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—,

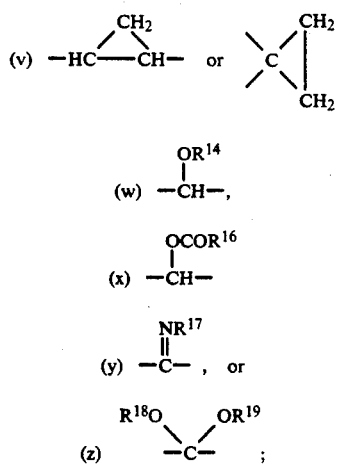

(v) —HC——CH— or [cyclopropyl structure]

(w) —CH—
     |
     OR$^{14}$ (x) —CH—
     |
     OCOR$^{16}$ (y) —C— , or
     ‖
     NR$^{17}$ (z) —C—
     / \
   R$^{18}$O  OR$^{19}$
     ;

r is 1 or 2; and
the pharmaceutically acceptable salts thereof.

The terms "alkyl," "alkynyl," and the like include both the straight chain and branched chain species of these generic terms wherein the number of carbon atoms in the species permit. Unless otherwise noted, the specific names for these generic terms shall means the straight chain species. For example, the term "butyl" shall mean the normal butyl substituent, n-butyl.

One embodiment of the compounds of formula (I) are those compounds wherein:

$R^1$ is
(a) —CO$_2$R$^4$,

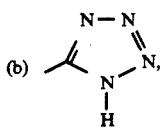

(b) [tetrazole structure with N—N, N, N, H]

(c) —NH—SO$_2$R$^{22}$,
(d) —CH$_2$SO$_2$NH-heteroaryl,
(e) —SO$_2$NH—CO—R$^{22}$,
(f) —CH$_2$SO$_2$NH—CO—R$^{22}$,
(g) —CONH—SO$_2$R$^{22}$,
(h) —CH$_2$CONH—SO$_2$R$^{22}$,
(i) —NHSO$_2$NHCO—R$^{22}$, or
(j) —NHCONHSO$_2$—R$^{22}$, $R^{2a}$ is H;
$R^{2b}$ is H, F, Cl, CF$_3$, C$_1$-C$_6$-alkyl, C$_2$-C$_6$-alkenyl, C$_2$-C$_6$-alkynyl, or aryl;
$R^{3a}$ is H;
$R^{3b}$ is H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is a single bond, —O— or —S—;
$R^6$ is
(a) C$_1$-C$_5$ alkyl or substituted C$_1$-C$_5$ alkyl with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F,
(b) C$_2$-C$_5$-alkenyl or C$_2$-C$_5$-alkynyl, or
(c) C$_3$-C$_5$-cycloalkyl;

$R^7$ is
(a) H, (b) C$_1$-C$_6$-alkyl or substituted C$_1$-C$_6$-alkyl with a —OH, —N(R$^4$)$_2$, —NR$^4$COR$^{22}$ —NR$^4$CO$_2$R$^{22}$, —NR$^4$CONR$^4$R$^{22}$ substituent, or
(c) aryl or substituted aryl with a Cl, —F, —O(C$_1$-C$_4$-alkyl), —CO$_2$R$_4$, —SO$_2$R$^4$ substituent;

$R^{8a}$ and $R^{8b}$ are independently
(a) H,
(b) C$_1$-C$_8$-alkyl or substituted C$_1$-C$_8$-alkyl with COOR, OCOR$^{4a}$, OH, aryl, or —(CH$_2$)$_{1-4}$R$^4$ substituent,
(c) OR$^{22}$,
(d) —OH,
(e) —NO$_2$,
(f) —N(R$^{22a}$)COR$^{22}$,
(g) —CONR$^4$R$^{22}$,
(h) —N(R$^{22a}$)CO$_2$R$^{22}$,
(i) —NR$^4$R$^{22}$,
(j) Cl, F, or Br,
(k) —CF$_3$,
(l) —CO$_2$R$^{4a}$,
(m) —CO-aryl,
(n) —S(O)$_x$—R$^{22}$,
(o) —SO$_2$—NR$^4$R$^9$,
(p) —N(R$^{22a}$)SO$_2$R$^{22}$,
(q) aryl,
(r) —N(R$^{22a}$)CONR$^4$R$^{22}$, or
(s) —N(R$^{22a}$)SO$_2$N(R$^4$)R$^{22}$;

X is a single bond; and
r is one.

In a class of this embodiment are those compounds of Formula (I) wherein:
A-B-C together with the pyrimidinone to which it is attached form a member selected from the group:

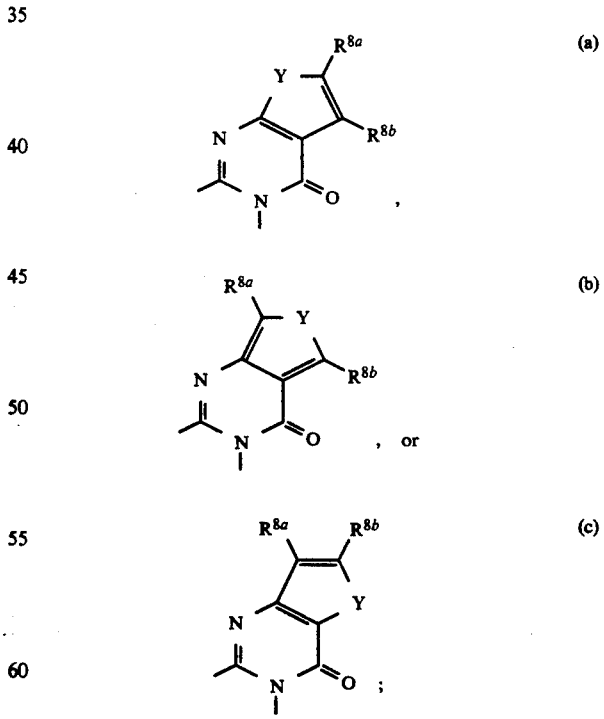

E is a single bond;
$R^{2b}$ and $R^{3b}$ are H;
$R^6$ is C$_1$-C$_4$ alkyl, C$_2$-C$_5$ alkenyl, cyclopropyl, —CH$_2$CH$_2$CF$_3$, —CH$_2$CH$_2$CH$_2$CF$_3$ or cyclopropylmethyl; and $R^{8a}$ and $R^{8b}$ are each independently H, —$C_1$-$C_4$ alkyl, —$NO_2$, —$NR^4R^{22}$, —$OCH_3$, —$NR^{22a}COOR^{22}$, —Cl, $CH_2COOR^{4a}$, —$S(O)_x$—$R^{22}$, —$NR^{22a}CONR^4R^{22}$, —$CH_2OCO(C_1$-$C_4$-alkyl), —$NR^{22a}COR^{22}$, —$CO_2R^{4a}$, —F, —$CH_2Ph$, or —$CONR^4R^{22}$.

Illustrative of this class are the following compounds:
(1) 2-n-Butyl-3-[(2'-(tetrazol-5-yl)biphen-4-yl)-methyl]-furo{3,4-d}pyrimidin-4(3H)-one;
(2) 5-Isopropyl-2-n-propyl-3-[(2'-(tetrazol-5-yl)-biphen-4-yl)-methyl]furo{3,4-d}pyrimidin-4(3H)-one;
(3) 2-Butyl-3-[(2'-carboxybiphen-4-yl)-methyl]-thieno{3,4-d}pyrimidin-4(3H)-one;
(4) 2-Butyl-3-[(2'-(tetrazol-5-yl)biphen-4-yl)-methyl]-thieno{3,4-d}pyrimidin-4(3H)-one;
(5) 5-Isopropyl-2-n-propyl-3-[(2'-tetrazol-5-yl)-biphen-4-yl)-methyl]thieno{3,4-d}pyrimidin-4(3H)-one;
(6) 2-n-Butyl-3-[(2'-carboxybiphen-4-yl)-methyl]-furo{2,3-d}pyrimidin-4(3H)-one;
(7) 2-n-Propyl-3-[(2'-(tetrazol-5-yl)biphen-4-yl)-methyl]-furo{2,3-d}pyrimidin-4(3H)-one;
(8) 5-Isopropyl-2-n-propyl-3-[(2'-(tetrazol-5-yl)-biphen-4-yl)-methyl]furo{2,3-d}pyrimidin-4(3H)-one;
(9) 5-(N-Benzoyl-N-n-pentyl)amino-2-n-propyl-3-[(2'-(tetrazol-5-yl)biphen-4-yl)-methyl]furo{2,3-d}pyrimidin-4(3H)-one;
(10) 2-n-Butyl-5-methyl-3-[(2'-(tetrazol-5-yl)-biphen-4-yl)-methyl]thieno{2,3-d}pyrimidin-4(3H)-one;
(11) 5-(N-Benzyl-N-n-butloxycarbonyl)amino-2-n-propyl-3-[(2'-tetrazol-5-yl)biphen-4-yl)-methyl]-thieno{2,3-d}pyrimidin-4(3H)-one;
(12) 5-(N-(4-Fluoro-benzyl)-N-n-butyl)amino-2-n-propyl-3-[(2'-tetrazol-5-yl)-biphen-4-yl)-methyl]-thieno{2,3-d}pyrimidin-4(3H)-one;
(13) 6-Isopropyl-2-ethyl-3-[(2'-((4-fluorobenzoylamino)sulfonyl)-(1,1'-biphenyl)-4-yl)methyl]-thieno{2,3-d}pyrimidin-4(3H)-one;
(14) 5-(N-(Benzoyl)-N-n-pentyl)amino-2-n-ethyl-3-[(2'-(tetrazol-5-yl)biphen-4-yl)-methyl]thieno{2,3-d}pyrimidin-4(3H)-one;
(15) 5-(N-Methyl-N-isopropylcarbamoyl)-amino-2-propyl-[(2'-((benzoylamino)sulfonyl)-(1,1'-biphenyl)-4-yl)-methyl]thieno{2,3-d}pyrimidin-4(3H)-one;
(16) 2-Butyl-5-carboxy-3-[(2'-(tetrazol-5-yl)biphen-4-yl)-methyl]thieno{2,3-d}pyrimidin-4(3H)-one;
(17) 2-Propyl-3-[(2'-(tetrazol-5-yl)biphen-4-yl)methyl]-pyrrolo(3,2-d)-pyrimidin-4(3H)-one;
(18) 2-Propyl-7-(2-benzylhexyl)-3-[(2'-(tetrazol-5-yl)biphen-4-yl)-methyl]pyrrolo(3,2-d)-pyrimidin-4(3H)-one;
(19) 2-Cyclopropyl-7-Phenyl-[(2'-((benzoylamino)sulfonyl)-(1,1'-biphenyl)-4-yl)methyl]pyrrolo(3,2-d)-pyrimidin-4(3H)-one;
(20) 2-Butyl-5-isobutyl-3-[(2'-carboxybiphen-4-yl)methyl]pyrrolo(3,2-d)-pyrimidin-4(3H)-one;
(21) 6-Isopropyl-2-propyl-3-[(2'-(tetrazol-5-yl)biphen-4-yl)-methyl]pyrrolo(3,2-d)-pyrimidine-4(3H)-one;
(22) 5-Methyl-2-hexyl-3-[(2'-tetrazol-5-yl)biphen-4-yl)-methyl]pyrrolo(3,4-d)-pyrimidin-4(3H)-one;
(23) 6-Butyl-3-propyl-3]2'-carboxybiphen-4-yl)methyl]-pyrrolo(3,4-d)-pyrimidin-4(3H)-one;
(24) 7-Methyl-2-propyl-3-[(2'-(tetrazol-5-yl)biphen-4-yl)-methyl]pyrrolo(2,3-d)-pyrimidin-4(3H)-one;
(25) 5-Isopropyl-7-methyl-2-propyl-3-[(2'-(tetrazol-5-yl)biphen-4-yl)-methyl]pyrrolo(2,3-d)-pyrimidin-4(3H)-one;
(26) 5-(N-Methyl-(N-isopropyl-N-methyl-carbamoyl)amino-2-propyl-[(2'-((benzoylamino)sulfonyl)-(1,1'-biphenyl)-4-yl)methyl]pyrrolo(2,3-d)-pyrimidin-4(3H)-one;
(27) 2Ethyl-5-(N-(4-trifluoromethylbenzoyl)-N-n-pentyl)amino-3-[(2'-tetrazol-5-yl)biphen-4-yl)methyl]-pyrrolo(2,3-d)-pyrimidin-4(3H)-one;
(28) 2-Propyl-3-[(2'-tetrazol-5-yl)biphen-4-yl)methyl]-thieno{3,2-d}pyrimidin-4(3H)-one;
(29) 2-Propyl-6-isopropyl-7-methyl-3-[(2'-(tetrazol-5-yl)biphen-4-yl)methyl]thieno{3,2-d}pyrimidin-4(3H)-one;
(30) 2-Propyl-6-methyl-3-[(2'-(tetrazol-5-yl)biphen-4-yl)methyl]thieno{3,2-d}pyrimidin-4(3H)-one;
(31) 2-n-Butyl-3-[(2'-(tetrazol-5-yl)biphen-4-yl)methyl]-furo{3,2-d}pyrimidin-4(3H)-one;
(32) 2-Cyclopropyl-3-[(2'-(tetrazol-5-yl)biphen-4-yl)methyl]furo{3,2-d}pyrimidin-4(3H)-one;
(33) 7-Methyl-2-n-propyl-3-[(2'-(tetrazol-5-yl)biphen-4-yl)methyl]furo{3,2-d}pyrimidin-4(3H)-one;
(34) 2-n-Butyl-3-[(2'-(tetrazol-5-yl)-biphen-4-yl)methyl]-thieno{3,2-d}pyrimidin-4(3H)-one; and
(35) 2-Butyl-3-[(2'-tetrazol-5-yl)-biphen-4-yl)methyl]-4,5,6,7-tetrahydrobenzo[b]thieno{2,3-d}pyrimidin-4(3H)-one.

Another class of this embodiment are those compounds of Formula (I) wherein:

A-B-C together with the pyrimidinone to which it is attached form a member selected from the groups:

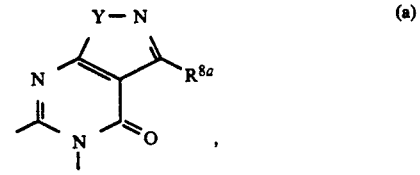
(a)

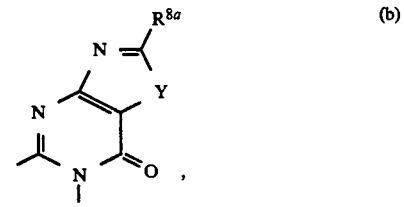
(b)

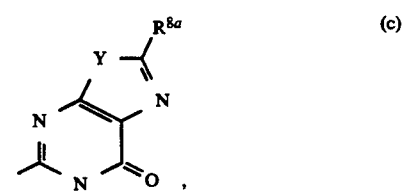
(c)

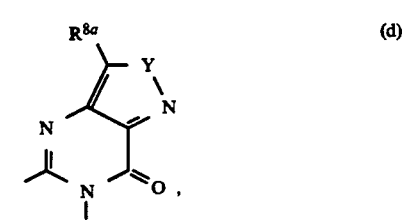
(d)

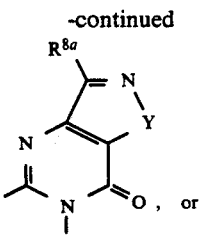

(e)

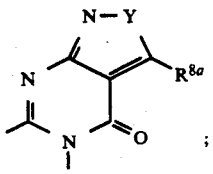

(f)

Y is O, S or NR$^7$;

R$^{2a}$, R$^{2b}$, R$^{3a}$, R$^{3b}$ are each independently H, C$_1$-C$_6$-alkyl; C$_2$-C$_6$-alkenyl, C$_2$-C$_6$-alkynyl, —Cl, —F, —NO$_2$, or —CF$_3$;

R$^6$ is C$_1$-C$_4$-alkyl, cyclopropyl, —CH$_2$CH$_2$CH$_2$CF$_3$, —CH$_2$CH$_2$CF$_3$, C$_2$-C$_5$-alkenyl, or cyclopropylmethyl;

R$^7$ is H or C$_1$-C$_6$ alkyl; and

R$^{8a}$ and R$^{8b}$ independently are: H, C$_1$-C$_4$-alkyl, —NO$_2$, —NR$^4$R$^{22}$, —OCH$_3$, —NR$^4$COOR$^{22}$, —Cl, CH$_2$COOR$^{4a}$, —S(O)$_x$—R$^{22}$, NR$^4$CONR$^4$R$^{22}$, CH$_2$OCO(C$_1$-C$_4$-alkyl), —NR$^4$COR$^{22}$, CO$_2$R$^{4a}$, —F, CH$_2$Ph, or —CONR$^4$R$^{22}$.

Illustrative compounds within this class are:

(1) 6-Cyclopropy-1,5-dihydro-5-[(2'-(tetrazol-5-yl)biphen-4-yl)-methyl]-4H-pyrazolo{3,4-d}pyrimidin-4-one;

(2) 1,5-Dihydro-1,3-dimethyl-6-propyl-5-[(2'-(tetrazol-5-yl)-biphen-4-yl)-methyl]-4H-pyrazolo-{3,4-d}pyrimidin-4-one;

(3) 6-Butyl-1,5-dihydro-3-isopropyl-5-[(2'-(tetrazol-5-yl)-biphen-4-yl)-methyl]-4H-pyrazolo{3,4-d}pyrimidin-4-one;

(4) 1,5-Dihydro-6-ethyl-3-(N-benzoyl-N-n-pentyl)amino-5-[(2'-tetrazol-5-yl)biphen-4-yl)-methyl]-4H-pyrazolo-{3,4-d}pyrimidin-4-one;

(5) 5-n-Butyl-1,6-dihydro-6-[(2'-carboxybiphen-4-yl)-methyl]-4H-pyrazolo{4,3-d}pyrimidin-7-one;

(6) 1,6-Dihydro-3-isopropyl-5-n-propyl-6-[(2'-(tetrazol-5-yl)-biphen-4-yl)-methyl]-4H-pyrazolo-{4,3-d}pyrimidin-7-one;

(7) 1-Benzyl-1,6-dihydro-5-n-propyl-6[(2'-(tetrazol-5-yl)biphen-4-yl)-methyl]-4H-pyrazolo{4,3-d}pyrimidin-7-one;

(8) 2-Butyl-1,7-dihydro-1-[(2'-(tetrazol-5-yl)biphen-4-yl)-methyl]-6H-purin-6-one;

(9) 1,7-Dihydro-2-propyl-1-[(2'-(tetrazol-5-yl)biphen-4-yl)-methyl]-6H-purin-6-one;

(10) 1,7-Dihydro-7-methyl-2-propyl-1-[(2'-(tetrazol-5-yl)biphen-4-yl)-methyl]-6H-purin-6-one;

(11) 1,9-Dihydro-9-Methyl-2-n-propyl-1-[(2'-(tetrazol-5-yl)-biphen-4-yl)-methyl]-6H-purin-6-one;

(12) 1,7-Dihydro-7-(4-fluorobenzyl)-2-n-propyl-1-[(2'-tetrazol-5-yl)-methyl]-6H-purin-6-one;

(13) 1,7-Dihydro-2-ethyl-8-(N-(4-fluoro-benzyl)-N-n-butyl)amino-1-[(2'-(tetrazol-5-yl)biphen-4-yl)methyl]-6H-purin-6-one;

(14) 1,7-Dihydro-2-butyl-8-isopropyl-1-[(2'-((benzoylamino)-sulfonyl)-(1,1'-biphenyl)-4-yl)methyl]-6H-purin-6-one;

(15) 1,9-Dihydro-8-isobutyl-7-methyl-2-n-propyl-1-[(2'-((3,6-dichloro-benzoylamino)sulfonyl)-(1,1'-biphenyl)-4-yl)methyl]-6H-purin-6-one;

(16) 1,9-Dihydro-9-methyl-2-n-propyl-8-trifluoromethyl-1-[(2'-(tetrazol-5-yl)biphen-4-yl)methyl]-6H-purin-6-one.

(17) 6-n-Butyl-5-[(2'-carboxybiphen-4-yl)-methyl]isothiazolo{3,4-d}pyrimidin-4(5H)-one;

(18) 3-Isopropyl-6-n-propyl-5-[(2'-(tetrazol-5-yl)biphen-4-yl)-methyl]isothiazolo{3,4-d}pyrimidin-4(5H)-one;

(19) 6-Ethyl-3-(N-isopropyloxycarbonyl-N-benzyl)amino-5-[(2'-(tetrazol-5-yl)biphen-4-yl)-methyl]isothiazolo{3,4-d}pyrimidin-4(5H)-one;

(20) 3-Methyl-6-n-propyl-5-[(2'-((3,6-dichlorobenzoylamino)sulfonyl)-(1,1'-biphenyl)-4-yl)-methyl]isothiazolo{3,4-d}pyrimidin-4(5H)-one;

(21) 5-n-Butyl-6-[(2'-carboxybiphen-4-yl)-methyl]isothiazolo{4,3-d}pyrimidin-7(6H)-one;

(22) 5-n-Propyl-6-[(2'-tetrazol-5-yl)-methyl]isothiazolo{4,3-d}pyrimidin-7(6H)-one;

(23) 3-Methyl-5-n-propyl-6-[(2'-(tetrazol-5-yl)biphen-4-yl)-methyl]isothiazolo}4,3-d}pyrimidin-7(6H)-one;

(24) 5-n-Propyl-6-[(2'-(tetrazol-5-yl)biphen-4-yl-methyl]isothiazolo{4,5-d}pyrimidin-7(6H)-one;

(25) 5-Isobutyl-6-[(2'-((benzoylamino)sulfonyl)-(1,1'-biphenyl)-4-yl)methyl]isothiazolo{4,5-d}pyrimidin-7(6H)-one;

(26) 5-Butyl-3-isopropyl-6-[(2'-(tetrazol-5-yl)biphen-4-yl)-methyl]isothiazolo}4,5-d}pyrimidin-7(6H)-one;

(27) 6-n-Propyl-5-[(2'-(tetrazol-5-yl)biphen-4-yl)-methyl]isothiazolo}5,4-d}pyrimidin-4(5H)-one;

(28) 3-Isopropyl-6-n-propyl-5-[(2'-(tetrazol-5-yl)biphen-4-yl)methyl]isothiazolo{5,4-d}pyrimidin-4(5H)-one;

(29) 6-Ethyl-3-methyl-5-[(2'-(tetrazol-5-yl)biphen-4-yl)-methyl]isothiazolo{5,4-d}pyrimidin-4(5H)-one;

(30) 6-n-Propyl-5-[(2'-((benzoylamino)sulfonyl)-(1,1'-biphenyl)-4-yl)methyl]isothiazolo{5,4-d}pyrimidin-4(5H)-one;

(31) 6-n-Butyl-5-[(2'-carboxybiphen-4-yl)-methyl]-isoxazolo{3,4-d}pyrimidin-4(5H)-one;

(32) 3-Isopropyl-6-n-propyl-5-[(2'-(tetrazol-5-yl)biphen-4-yl)-methyl]isoxazolo{3,4-d}pyrimidin-4(5H)-one;

(33) 3-(N-Isopropyloxycarbonyl-N-benzyl)amino-6-ethyl-5-[(2'-(tetrazol-5-yl)biphen-4-yl)-methyl]isoxazolo{3,4-d}pyrimidin-4(5H)-one;

(34) 6-n-Propyl-3-methyl-5-[(2'-((3,6-dichloro-benzoylamino)sulfonyl)-(1,1'-biphenyl)-4-yl)methyl]isoxazolo{3,4-d}pyrimidin-4(5H)-one;

(35) 5-n-Butyl-6-[(2'-carboxybiphen-4-yl)-methyl]isoxazolo{4,3-d}pyrimidin-7(6H)-one;

(36) 5-n-Propyl-6-[(2'-(tetrazol-5-yl)biphen-4-yl)-methyl]isoxazolo{4,3-d}pyrimidin-7(6H)-one;

(37) 5-n-Propyl-3-methyl-6-[(2'-(tetrazol-5-yl)biphen-4-yl)-methyl]isoxazolo{4,3-d}pyrimidin-7(6H)-one;

(38) 5-n-Propyl-6-[(2'-(tetrazol-5-yl)biphen-4-yl)-methyl]isoxazolo{4,5-d}pyrimidin-7(6H)-one;

(39) 5-Isobutyl-6-[(2'-((benzoylamino)sulfonyl)-(1,1'-biphenyl)-4-yl)methyl]isoxazolo{4,5-d}pyrimidin-7(6H)-one;

(40) 5-n-Butyl-3-isopropyl-6-[(2'-(tetrazol-5-yl)biphen-4-yl)methyl]isoxazolo{4,5-d}pyrimidin-7(6H)-one;

(41) 6-n-Propyl-5-[(2'-(tetrazol-5-yl)biphen-4-yl)-methyl]isoxazolo{5,4-d}pyrimidin-4(5H)-one;

(42) 3-Isopropyl-6-n-propyl-5-[(2'-(tetrazol-5-yl)biphen-4-yl)-methyl]isoxazolo{5,4-d}pyrimidin-4(5H)-one;

(43) 6-Ethyl-3-methyl-5-[(2'-(tetrazol-5-yl)biphen-4-yl)-methyl]isoxazolo{5,4-d}pyrimidin-4(5H)-one;
(44) 5-n-Propyl-6-[(2'-((benzoylamino)sulfonyl)-(1,1'-biphenyl)-4-yl)methyl]isoxazolo{4,5-d}pyrimidin-7(6H)-one;
(45) 5-n-Propyl-6-[(2'-(tetrazol-5-yl)biphen-4-yl)-methyl]thiazolo{4,5-d}pyrimidin-7(6H)-one;
(46) 2-Methyl-5-n-propyl-6-[(2'-(tetrazol-5-yl)biphen-4-yl)-methyl]thiazolo{4,5-d}pyrimidin-7(6H)-one;
(47) 5-n-Propyl-2-isopropyl-6-[(2'-(tetrazol-5-yl)biphen-4-yl)-methyl]thiazolo{4,5-d}pyrimidin-7(6H)-one;
(48) 5-Ethyl-2-phenyl-6-[(2'-((benzoylamino)sulfonyl)-(1,1'-biphenyl)-4-yl)methyl]thiazolo{4,5-d}pyrimidin-7(6H)-one;
(49) 5-Butyl-2-(4-pyridyl)-6-[(2'-((4-fluorobenzoylamino)sulfonyl)-(1-1'-biphenyl)-4-yl)methyl]-thiazolo{4,5-d}pyrimidin-7(6H)-one;
(50) 5-n-Butyl-6-[(2'-tetrazol-5-yl)biphen-4-yl)-methyl]-thiazolo{5,4-d}pyrimidin-7(6H)-one;
(51) 5-n-Propyl-6[(2'-carboxybiphen-4-yl)-methyl]-thiazolo{5,4-d}pyrimidin-7(6H)-one;
(52) 5-n-Propyl-2-trifluoromethyl-6-[(2'-(tetrazol-5-yl)biphen-4-yl)-methyl]thiazolo{5,4-d}pyrimidin-7(6H)-one;
(53) 5-n-Propyl-2-isopropyl-6[(2'-tetrazol-5-yl)biphen-4-yl)-methyl]thiazolo{5,4-d}pyrimidin-7(6H)-one;
(54) 5-Ethyl-2-carboxy-6-[(2'-((benzoylamino)sulfonyl)-(1,1'-biphenyl)-4-yl)methyl]thiazolo{5,4-d}-pyrimidin-7(6H)-one;
(55) 5-Butyl-2-hydroxymethyl-6-[(2'-((fluorobenzoylamino)sulfonyl)-(1,1'-biphenyl)-4-yl)methyl]-thiazolo{5,4-d}pyrimidin-7(6H)-one;
(56) 5-n-Propyl-6-[(2'-(tetrazol-5-yl)biphen-4-yl)methyl]oxazolo{4,5-d}pyrimidin-7(6H)-one;
(57) 5-n-Propyl-2-methyl-6-[(2'-(tetrazol-5yl)biphen-4-yl)-methyl]oxazolo{4,5-d}pyrimidin-7(6H)-one;
(58) 5-n-Propyl-2-isopropyl-6-[(2'-(tetrazol-5-yl)biphen-4-yl)-methyl]oxazolo{4,5-d}pyrimidin-7(6H)-one;
(59) 5-ethyl-2-phenyl-6-[(2'-((benzoylamino)sulfonyl)-(1-1'-biphenyl)-4-yl)methyl]oxazolo{4,5-d}-pyrimidin-7(6H)-one;
(60) 5-Butyl-2-(4-pyridyl)-6-[(2'-((fluorobenzoylamino)-sulfonyl)-(1,1'-biphenyl)-4-yl)methyl[oxazolo{4,5-d}pyrimidin-7(6H)-one;
(61) 5-n-Butyl-6-[(2'-(tetrazol-5-yl)biphen-4-yl-methyl-]oxazolo{5,4-d}pyrimidin-7(6H)-one;
(62) 5-n-Propyl-6-[(2'carboxybiphen-4-yl)-methyl]oxazolo{5,4-d}pyrimidin-7(6H)-one;
(63) 5-n-Propyl-2-trifluoromethyl-6[(2'-(tetrazol-5-yl)biphen-4-yl)-methyl]oxazolo{5,4-d}pyrimidin-7(6H)-one;
(64) 5-n-Propyl-2-isopropyl-6-[(2'-(tetrazol-5-yl)biphen-4-yl)-methyl]oxazolo{5,4-d}pyrimidin-7(6H)-one;
(65) 5-Ethyl-2-carboxy-6-[(2'-((benzoylamino)sulfonyl)-(1-1'-biphenyl)-4-yl)methyl]oxazolo{5,4-d}pyrimidin-7(6H)-one;
(66) 5-Butyl-2hydroxymethyl-6-[(2'-((fluorobenzoylamino)sulfonyl)-(1-1'-biphenyl)-4-yl)methyl]oxazolo{5,4-d}pyrimidin-7(6H)-one; and
(67) 2,5-Dihydro-2-isopropyl-5-[(2'-(tetrazol-5-yl)-biphen-4-yl)-methyl]-4H-pyrazolo{3,4-d}pyrimidin-4-one.

In naming compounds of Formula (I) which contain a biphenylmethyl substituent, it should be noted that the following two names for compound (i) shown below are considered to be equivalent:

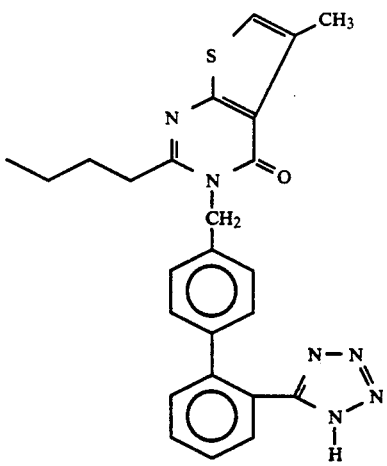

(1) 2-n-Butyl-5-methyl-3-[(2'-(tetrazol-5-yl)biphen-4-yl)methyl]thieno[2,3-d]pyrimidin-4-(3H)-one; or,
(2) 2-n-Butyl-5-methyl-3-[(2'-(tetrazol-5-yl)[1,1']biphenyl-4-yl)methyl]thieno[2,3-d]pyrimidin-4(3H)-one.

ABBREVIATIONS USED IN SCHEMES

| | |
|---|---|
| DMAP | Dimethylaminopyridine |
| —OTs | p-Toluenesulphonate |
| —OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

REFERENCES CITED IN SCHEMES

1. *The Chemistry of Heterocyclic Compounds-Fused Pyrimidines*, Part 1-The Quinazolines, W. L. F. Armarego, Interscience Publishers, New York, 1967
2. "Quinazolines"., W. L. F. Armarego, *Adv. in Het Chem.*, Vol 24, Pg 1, 1979.
3. For pyrroles: R. Boehm, R. Pech, *Pharmazie*, 245, 1990.
4. For pyrazoles: C. C. Cheng, R. K. Robins, *J. Org. Chem.*, 191, 1958.
5. For furan: S. S Sangapure, Y. S. Agasimundin, *J. Ind. Chem.* 627, 1978.
6. For pyrazoles and thiophenes: Smithkline Beckman Corp EP-349-239-A.
7. For thiophenes: C. J. Shishoo, M. B. Devani, K. S. Bhadti, S. Mohan, L. T. Patel, *Indian J. Chem.*, 1039, 1989.
8. For isothiazolo{5,4-d}pyrimidinone: S. Rujappa, B. G. Advani, R. Speenivsain., *Ind. J. Chem.*, 391, 1976.
9. For thiophene, furan, pyrrole: K. G. Dave, C. J. Shishov, M. B. Devani, R. Kalyanaraman, S. Ananthan, G. V. Ullas, V. S. Bhadti, *J. Het. Chem.*, 1497, 1980.
10. For purines: A. Yamazaki, I. Kumashiro, T. Takenishi, *J. Org. Chem.*, 3258, 1967.
11. For isothiazolo{4,5-d} and {4,3-d}pyrimidinone: A Holland, R. Slack T. F. Warren, D. Buttimore, *J. Chem. Soc.* 7277, 1965.
12. For pyrazoles: R. Bohm, *Pharmazie*, 45, 282, 1990.

13. For thiophene: M. S. Manhas, S. D. Sharma, S. G Amin, *J. Med. Chem.* 106, 1971.
14. For purines: *Comprehensive Heterocyclic Chemistry*, A. R. Katrizky and C. Rees. Volume 5, Pg 567.
15. For purines: Bergman and Tumari, *J. Chem Soc.* 4468, 1961.
16. For purines: *Heterocyclic Compounds, Fused Pyrimidines*, Part 2-purines by J. H. Lister. Wiley-Interscience, New York, 1971.
17. For purines: E. Richter, J. E. Loeffler, E. C. Taylor, *J. Am. Chem. Soc.*, 3144, 1959.
18. For furans: J. P. Marquet, J. A. Louisfert, E. Bisagni. *Bull Soc. Chim, France,* 4344, 1969.
19. *Chem Scripta,* 135, 1981.
20. For pyrroles: T. Murata, T. Sugawara, K. Ukawa., *Chem. Pharm. Bull.,* 26, 3083, 1978.
21. For oxazolo{5,4-d}pyrimidin-7(6H)-ones: V. D. Patil, L. B. Townsend, *J. Het. Chem.*, 503, 1971.
22. For oxazolo(4,5-d)pyrimidin-7(6H)-ones: M. Sekiya, J. Suzuki., *Chem Pharm Bull.*, 2242, 1970.

General information on the synthesis of quinazolinones may be found in several reference works. [1,2] Much of the chemical properties of the quinazolinone structural class may be applied to the preparation and modification of compounds of Formula (I).

The preparation of the pyrimidin-4(3H)-ones (2) fused to a desired heterocycle where E is a single bond may be achieved via several methods (Scheme 1) Treatment of a vicinally substituted amino nitrile such as (3) with an acid chloride, tertiary base and acyl chloride will give an amide.

Hydrolysis of the nitrile with basic hydrogen peroxide will give, following heating, the desired pyrimidinone heterocycle (2)[3,4,5]. Alternatively, when a vicinally substituted amino ester or carboxylic acid (4) is treated with an imidate ester under acidic or basic conditions, conversion to the pyrimidinone (2) occurs. [6,7,8,9] Furthermore, vicinally substituted amino amides such as (5) may be condensed with an orthoacetate to give (3) [10,11].

SCHEME 1

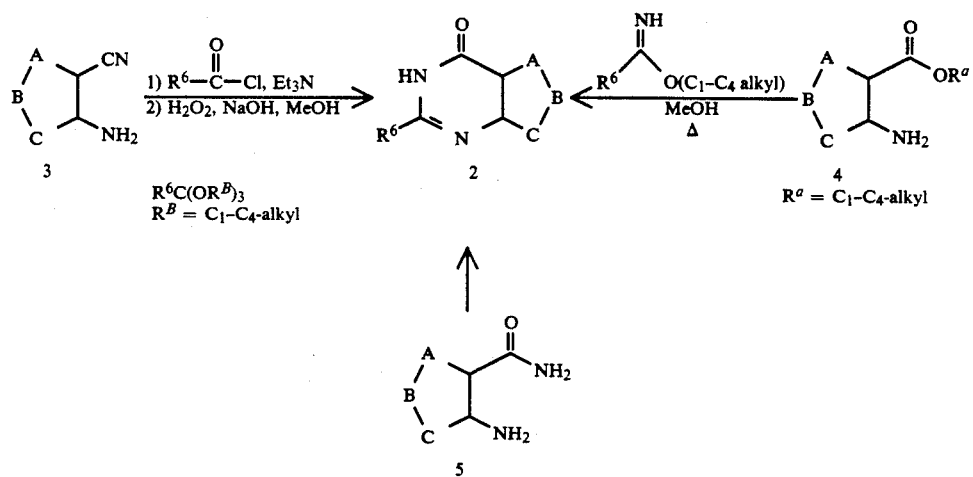

The compounds of Formula (I) can be synthesised using the reactions and techniques described below. The reactions are performed in a solvent appropriate to the reagents and materials employed and suitable for the transformation being effected. It is understood by those skilled in the art of organic synthesis that the functionality present on the heterocycle and other parts of the structure should be consistent with the chemical transformations proposed. Depending upon the reactions and techniques employed, this may involve changing the order of the synthetic steps, the use of required protecting groups followed by deprotection and, depending upon the particular pyrimidinone fused heterocycle being formed, the use of different strategies may be employed regarding the cyclization steps and the particular starting materials utilized.

The preparation of compounds of Formula (I) where r=1 may be achieved through the alkylation of the heterocycle (3) under appropriate basic conditions with a benzylic halide (6) (Scheme 2). The method used in any particular system will depend on the heterocycle in question, whether it is protected or not and the state of functionalization of the heterocycle. The choice of alkylative conditions will depend also on the particular regiochemistry of alkylation on the heterocycle. Changes in solvent, base, temperature and overall reaction methodology may control the observed alkylating regiochemistry. Any protecting groups on the $R^1$ moiety can be removed under appropriate conditions. Alternatively, the $R^1$ group may be constructed using techniques known to those skilled in the art.

SCHEME 2

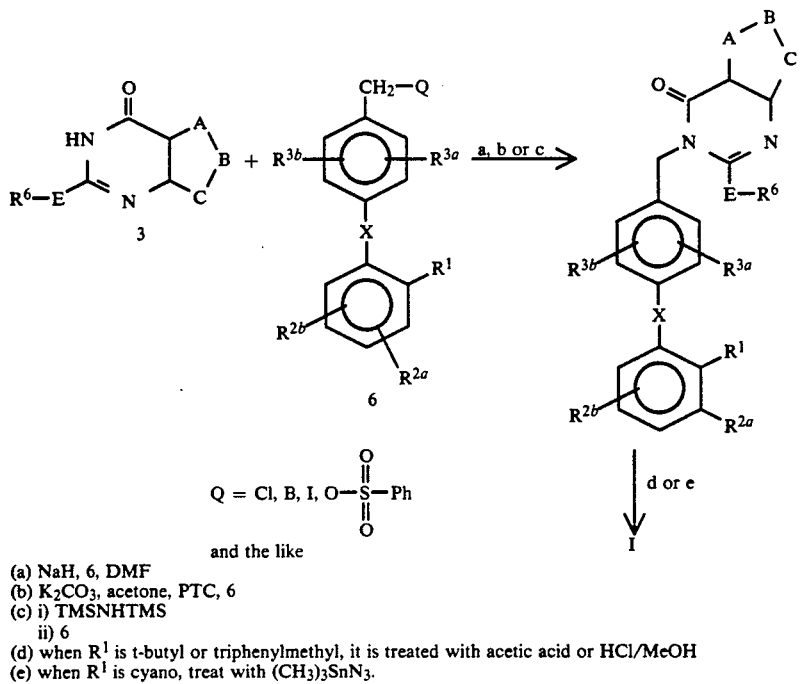

Q = Cl, B, I, O—S(=O)₂—Ph
and the like (a) NaH, 6, DMF
(b) K₂CO₃, acetone, PTC, 6
(c) i) TMSNHTMS
    ii) 6
(d) when R¹ is t-butyl or triphenylmethyl, it is treated with acetic acid or HCl/MeOH
(e) when R¹ is cyano, treat with (CH₃)₃SnN₃.

SCHEME 3

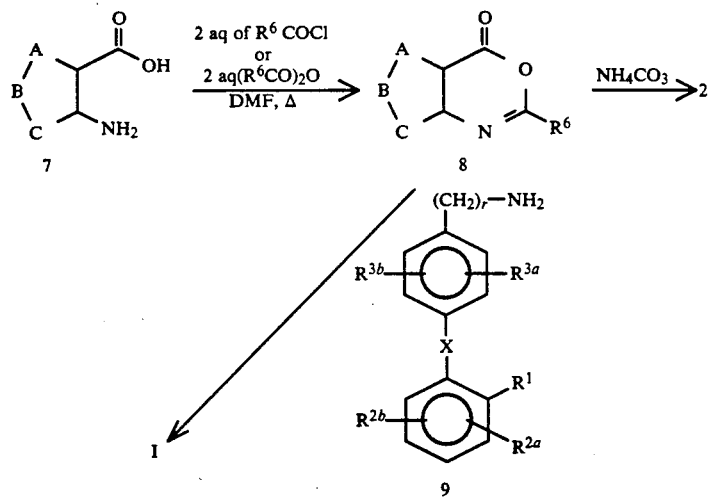

In cases where r=1 or 2 the method described above may not be suitable due to elimination or lack of reactivity. As an alternative (Scheme 3), a vicinal amino carboxylic acid (7) may be treated with two equivalents of an acylating reagent in a polar aprotic solvent in the presence of a tertiary amine base to give, after heating, the benzoxazine (8). (12,,13) Addition of an amine of general formula (9) and heating in the presence or absence of base will give the product of formula (I) after appropriate deprotection. Furthermore, addition of solid ammonium carbonate to the reaction mixture in place of the amine (9) will give rise to the pyrimidinone (2).

The benzyl halides (6) including the more preferred alkylating agents (6a and 6b, Scheme 4) can be prepared as described in European Patent Applications 253,310 and 291,969 and the references cited therein. However, a preferred method to prepare the biphenyl precursors (10a), (10b) and (10c) using Ni(O) or Pd(O) catalyzed cross-coupling reaction [E. Negishi, T. Takahashi, and A. O. King, Org. Synthesis, 66, 67 (1987)] is outlined in Scheme 4. As shown in Scheme (4), treatment of 4-bromotoluene (11) with t-BuLi, followed by the addition of a solution of ZnCl₂, produces the organo-zinc compound (12). Compound (12) is then coupled with (13a) or (13b) in the presence of Ni(PPh₃)₂Cl₂ catalyst to produce the desired biphenyl compound 10a or 10b (PPh₃=triphenylphosphine). Similarily, 1-iodo-2-nitrobenzene (13c) is coupled with organo-zinc compound (12) in the presence of Pd(PPh$_3$)$_4$ catalyst [prepared by treating Cl$_2$Pd(PPh$_3$)$_2$ with (i-Bu)$_2$AlH (2 equiv.)] to give the biphenyl compound (10c). These precursors, (10a), (10b) and (10c), are then transformed into halomethylbiphenyl derivatives (6a), (6b) and (6c), respectively, according to procedures described in European Patent Applications 253,310 and 291,969.

dures described in European Patent Applications 253,310 and 292,969.

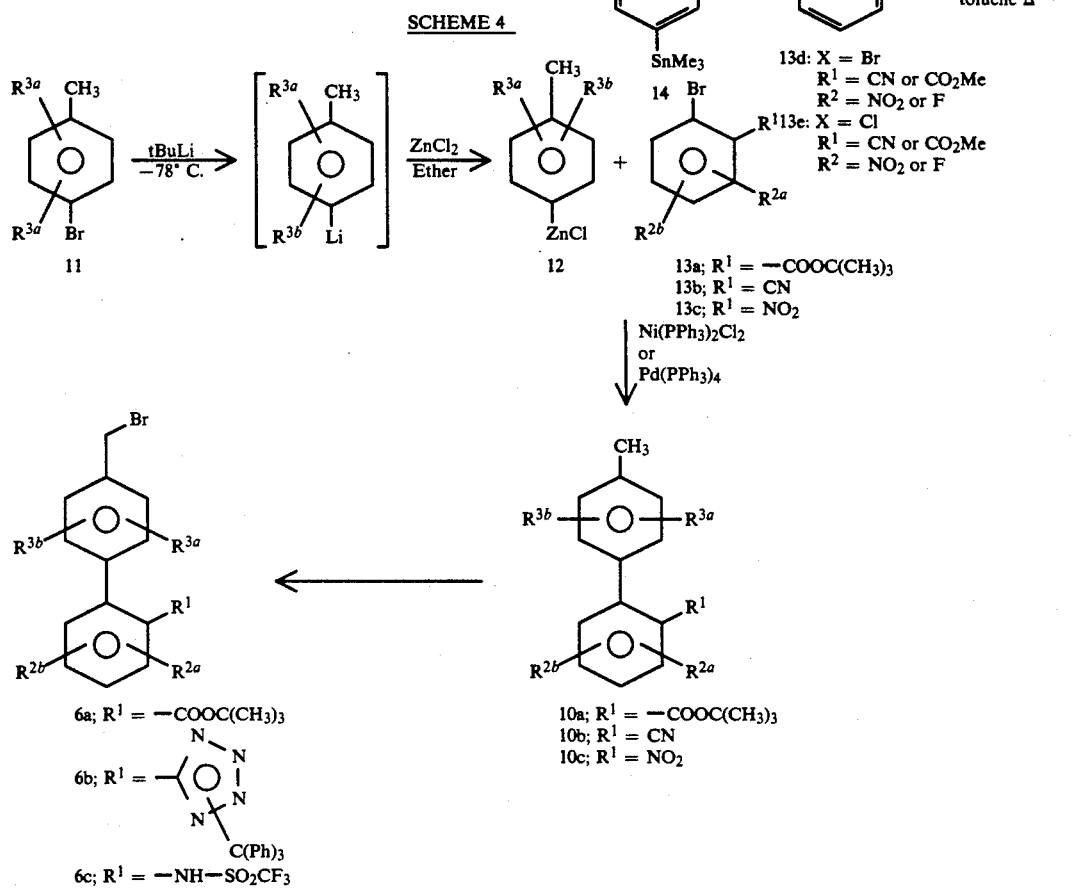

When there is additional substitution on the second phenyl ring (R$^{2a}$, R$^{2b}$ are not equal to hydrogen) the preferred method to prepare the biphenyl precursors (10d) and (10e), using the Pd(O) catalyzed cross-coupling reaction [J. K. Stille, *Angrew, Chem. Int. Ed. Engl.*, (25), 508 (1986)], is outlined in Scheme 4a. As shown in Scheme 4a, p-tolyltrimethyltin (14) is coupled with (13d) or (13e) in refluxing toluene in the presence of 5 mole % of Pd(PPh$_3$)$_4$ to produce the desired biphenyl compounds 10d and 10e. Table I illustrates the synthetic utility of this protocol. Compounds 10d (R$^2$=NO$_2$) and 10e (R$^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from (10d) (R$^2$=NO$_2$) and (10e) (R$^2$=NO$_2$) via reduction, formation of the diazonium tetrafluoroborate salt and thermal decomposition. These precursors (10d) (R$^2$=NO$_2$ or F or Cl) and 10e (R$^2$=NO$_2$ or F or Cl) are then transformed into the halomethyl biphenyl derivatives (6d) and (6e), respectively according to the procedures

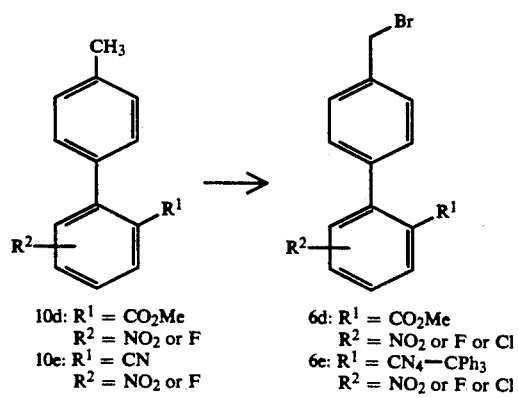

Biphenyl Synthesis Table 1

| X | R¹ | $R^a$ | $R^b$ | $R^c$ | $R^d$ | Product ($R^a$) | Rf (solvent) | Yield |
|---|---|---|---|---|---|---|---|---|
| Br | CO₂Me | NO₂ | H | H | H | 10d (3'-nitro) | 0.35(15:1 Hex/EtOAc) | 71% |
| Br | CN | H | NO₂ | H | H | 10e (4'-nitro) | 0.62(2× 6:1 Hex/EtOAc) | 74% |
| Br | CO₂Me | H | F | H | H | 10d (4'-fluoro) | 0.43(15:1 Hex/EtOAc) | 83% |
| Cl | CO₂Me | H | H | NO₂ | H | 10d (5'-nitro) | 0.22(15:1 Hex/EtOAc) | 70% |
| Br | CO₂Me | H | H | H | NO₂ | 10d (6'-nitro) | 0.24(15:1 Hex/EtOAc) | 79% |
| Br | CN | H | F | H | H | 10e (4'-fluoro) | 0.44(15:1 Hex/EtOAc) | 64% |
| Cl | CN | H | H | F | H | 10e (5'-fluoro) | 0.40(15:1 Hex/EtOAc) | 62% |

Compounds of formula (I) where R¹ is —CONH-SO₂R²² (where R²²=alkyl, aryl or heteroaryl) may be prepared from the corresponding carboxylic acid derivatives (14) as outlined in Scheme 5a. The carboxylic acid (14), obtained as described in Scheme 2 or Scheme 3, can be converted into the corresponding acid chloride by treatment with refluxing thionyl chloride or preferably with oxalyl chloride and a catalytic amount of dimethylformamide at low temperature [A. W. Burgstahler, L. O. Weigel, and C. G. Shaefer—*Synthesis*, 767, (1976)]. The acid chloride then can be treated with the alkali metal salt of R²²SO₂NH₂ to form the desired acylsulfonamide (15). Alternatively, these acylsulfonamides may be prepared from the carboxylic acids using N,N-diphenylcarbamoyl anhydride intermediates [F. J. Brown et al, European Patent Application, EP 199543; K. L. Shepard and W. Halczenko—*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide 15 [J. T. Drummond and G. Johnson, *Tetrahedron. Lett.*, 29, 1653 (1988)].

SCHEME 5a

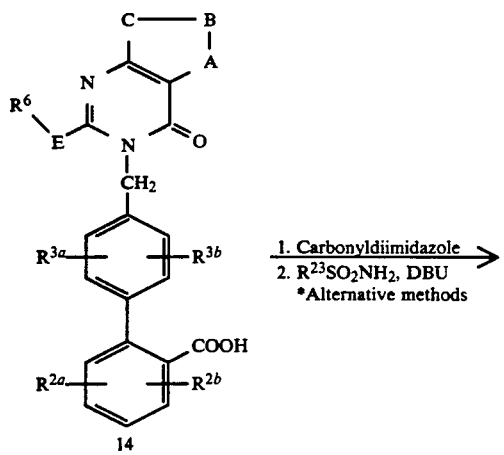

1. Carbonyldiimidazole
2. R²³SO₂NH₂, DBU

*Alternative methods

-continued
SCHEME 5a

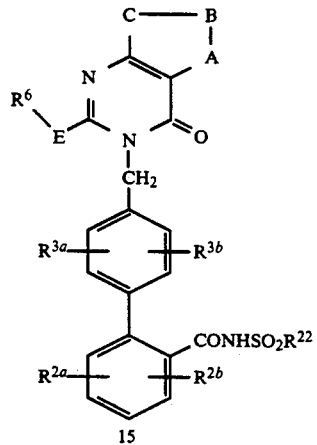

*Alternative Methods:
a) (i) SOCl₂, reflux
   (ii) R²²SO₂NH⁻M⁺ (where M is Na or Li)
b) (i) (COCl)₂-DMF, —20° C.
   (ii) R²²SO₂NH⁻M⁺
c) (i) N(N,N-Diphenylcarbamoyl)pyridinium chloride/aq. NaOH
   (ii) R²²SO₂NH⁻M⁺.

Compounds of formula (I) where R¹ is SO₂NH-COR²² may be prepared as outlined in Scheme 5b. The nitro compound, for example (10c) (prepared as described in Scheme 4), can be reduced to the corresponding amino compound and converted into aromatic diazoniun chloride salt, which then can be reacted with sulfur-dioxide in the presence of a copper (II) salt to form the corresponding arylsulfonyl chloride (16) [H. Meerwein, G. Dittmar, R. Gollner, K. Hafner, F. Mensch and O. Steifort, *Chem. Ber.*, 90, 841 (1957); A. J. Prinsen and H. Cerfontain, Recueil, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer. Chem. Soc.*, 63 (1941), 3446; E. H. Huntress and F. H. Carten, *J. Amer. Chem. Soc.*, 62, (1940), 511] to form the sulfonamide (17). The sulfonamide must then be protected preferably with the triphenylmethyl group by reaction with triphenylmethylchloride and triethylamine to give (18). The benzyl bromide (19) may be prepared from the sulfonamide (18), and then can be reacted with an alkali metal salt of an appropriate heterocyclic compound to form the key sulfonamide (20). Alternatively, 19 may be prepared as described in Scheme 5e. The sulfonamide (20) may be also prepared from the aromatic sulfonyl chloride (23) by treatment with ammonia. In addition, (23) may be prepared from the aryl amine (22) as outlined in Scheme 5c. The reaction of (23) with appropriate amines followed by acyl chlorides (or acyl-imidazoles or other acylating agents) may produce the desired acylsulfonamides (21).

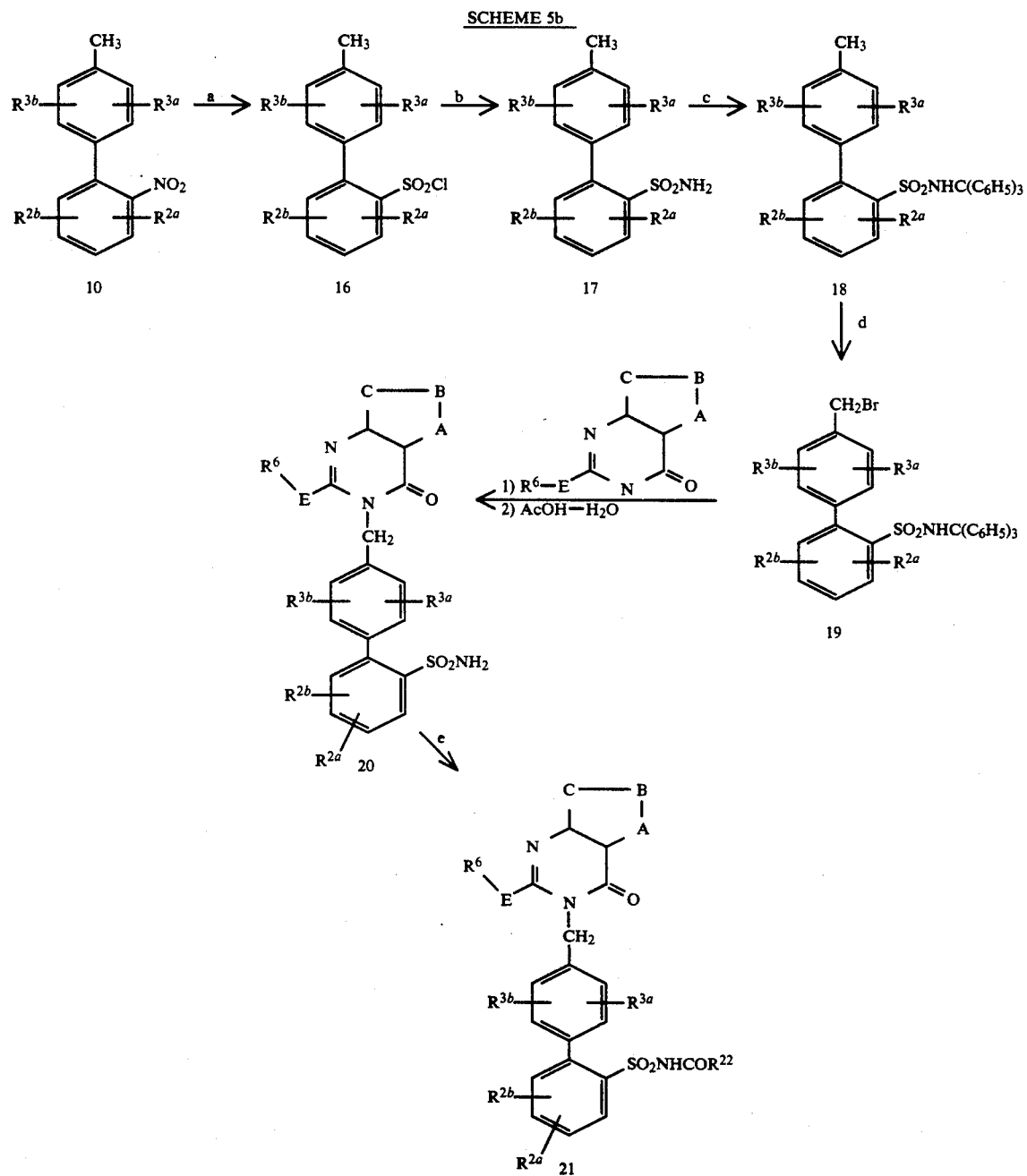

SCHEME 5b a. (i) $H_2$/Pd—C,
   (ii) $NaNO_2$—HCl,
   (iii) $SO_2$, AcOH, $CuCl_2$
b. $NH_3$ or $(NH_4)_2CO_3$
c. $(C_6H_5)_3CCl$, $Et_3N$, $CH_2Cl_2$, 25° C.
d. N-Bromosuccinimide
e. $R^{22}COCl$ or $R^{22}CO$—Im or other acylating agents.

The compounds bearing $R^1$ as $-SO_2NHR^{22}$ (where $R^{22}$ is heteroaryl) may be prepared by reacting the aromatic ring with chlorosulfonic acid [E. H. Huntress and F. H. Carten, *J. Amer. Chem. Soc.*, 62, 511 (1940)].

SCHEME 5c

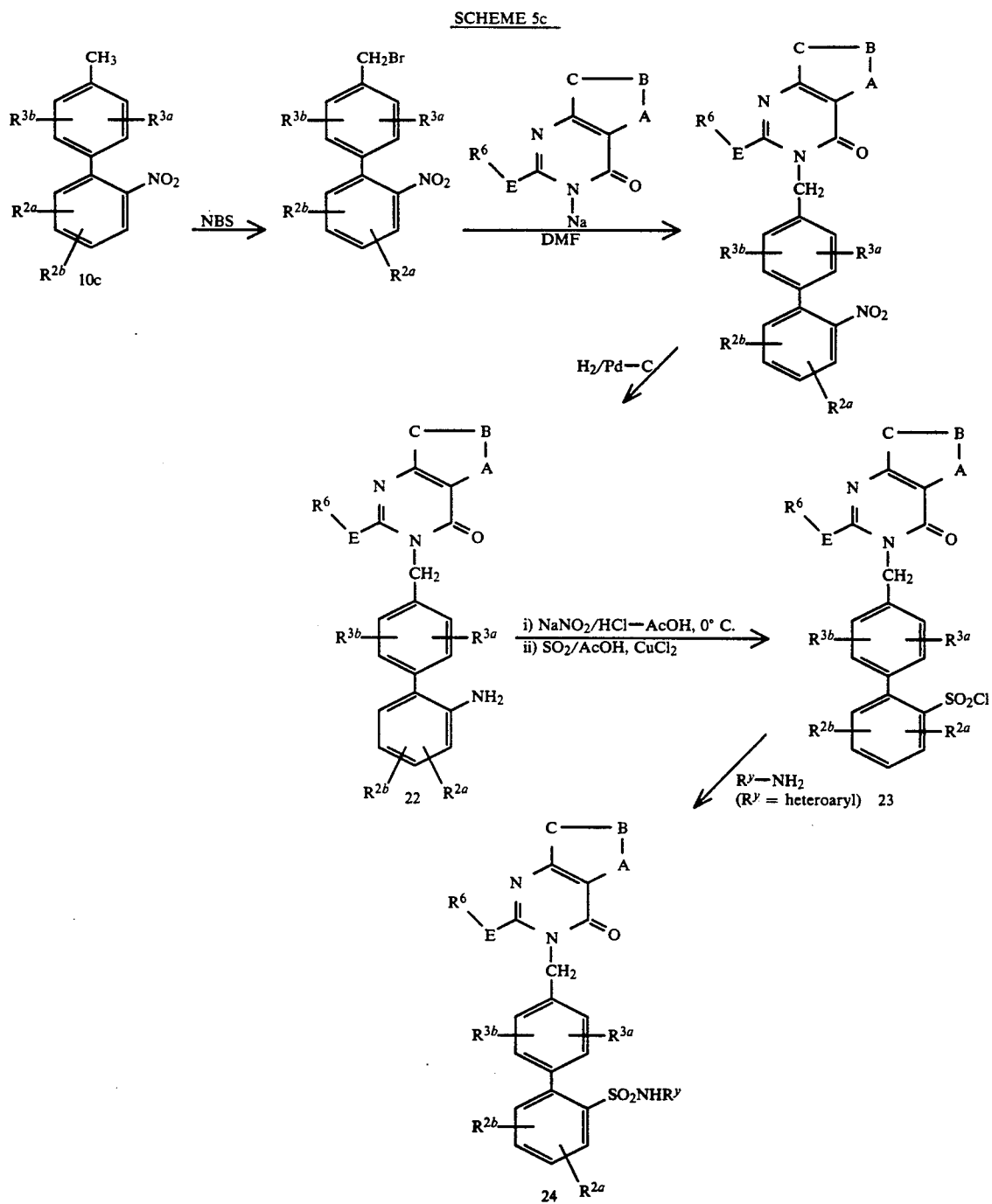

matic sulfonyl chloride (23) with appropriate heteroaryl amines as outlined in Scheme 5c to give (24). The sulfonyl chloride (23) may be prepared using similar chemistry to that outlined above. The sulfonyl chloride (23) may be the preferred intermediate for the synthesis of this class of compounds. The aromatic sulfonyl chlorides may also be prepared by reacting the sodium salt of aromatic sulfonic acids with $PCl_5$ or $POCl_3$ [C. M. Suter, *The Organic Chemistry of Sulfur*, John Wiley & Sons, 459, (1944)]. The aromatic sulfonic acid precursors may be prepared by chlorosulfonation of the aro- The biaryl sulfonamides (25) and (26) (described in Scheme 5b as (18)) can be prepared alternatively using palladium(O) catalyzed cross-coupling reactions of appropriate aryl-organotin precursors [J. K. Stille, *Pure Appl. Chem.*, 57, 1771 (1985); T. R. Baiely, *Tetrahedron Lett.*, 27, 4407 (1986); D. A. Widdowson and Y. Z. Zhang, *Tetrahedron*, 42, 2111 (1986)], as outlined in Scheme 5d. The organotin compound (27) [S. M. Moerlein, J. Organometallic Chem., 319, 29 (1987)], obtained from the aromatic precursor (28), may be coupled with aryl sulfonamide (29) and (30) using $Pd(PPh_3)_4$ or (PPh₃)₂PdCl₂ as catalysts to give biaryl sulfonamide (25) and (26). Similarly, the benzyl bromide (31) may be alternatively prepared from the appropriate organotin precursor (32) using the Pd(O) catalyzed cross-coupling reaction as outlined in Scheme 5e.

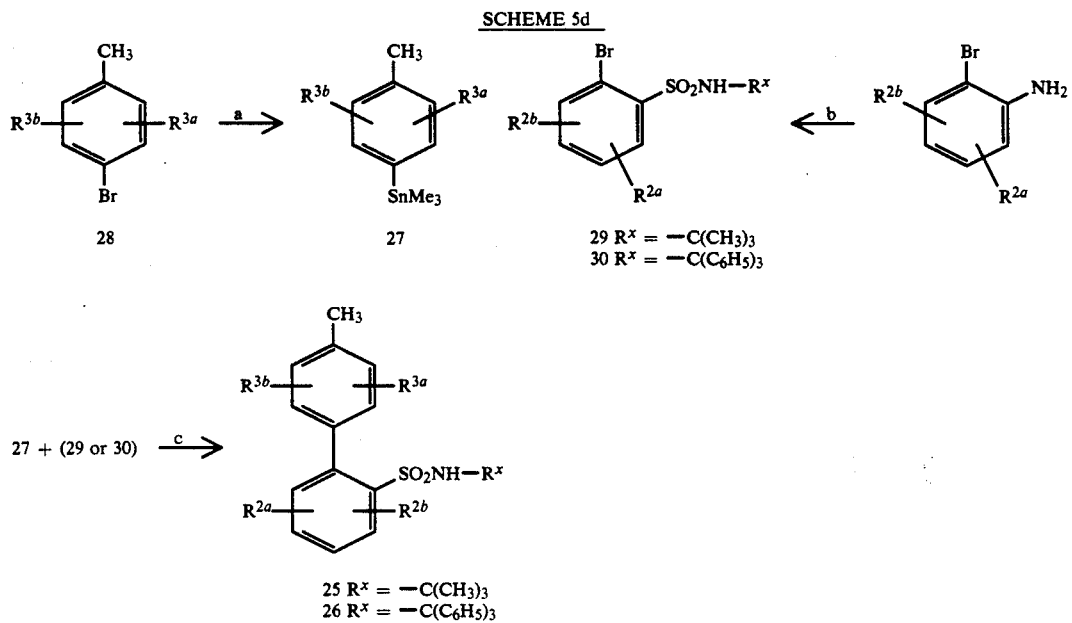

SCHEME 5d

29 R$^x$ = —C(CH₃)₃
30 R$^x$ = —C(C₆H₅)₃

25 R$^x$ = —C(CH₃)₃
26 R$^x$ = —C(C₆H₅)₃ a. (i) t-BuLi/ether, −78° C.
   (ii) Me₃SnCl
b. (i) NaNO₂/HCl
   (ii) SO₂, CuCl₂
   (iii) t-BuNH₂ or NH₃ followed by (C₆H₅)₃CCl
c. Pd(PPh₃)₄, Toluene, reflux or (PPh₃)₂PdCl₂, DMF, 90° C.

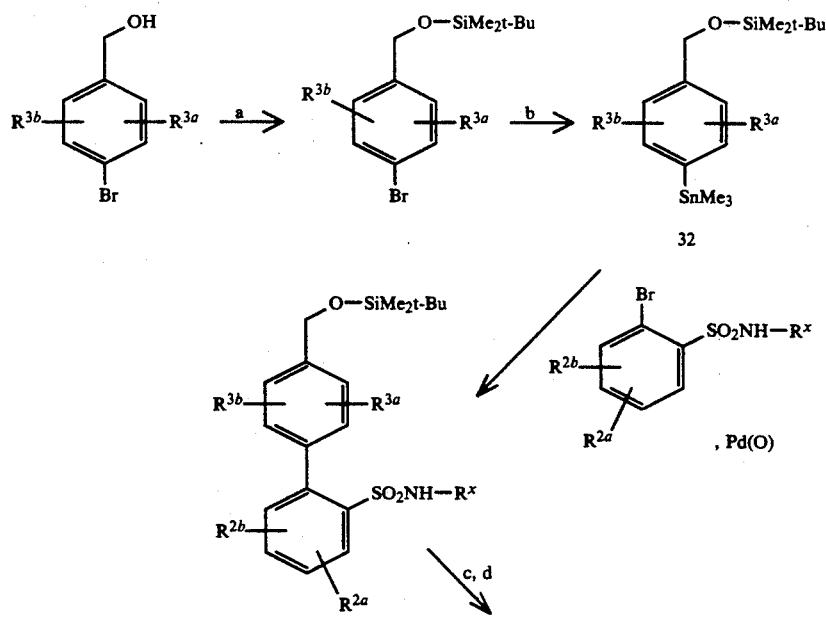

SCHEME 5e

SCHEME 5e -continued

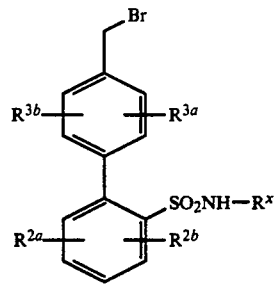

31a [R^x = —C(C_6H_5)_3]
31b [R^x = —C(CH_3)_3]

a. t-BuMe_2Si—Cl/Imidazole, DMF
b. t-BuLi, —78° C., Me_3SnCl
c. Tetrabutylammonium fluoride
d. CBr_4/Ph_3P.

The compounds bearing $R^1$=—$CH_2SO_2NHCOR^{22}$ and —$CH_2SO_2NHR^{22}$ may be prepared as outlined in Scheme 5f. The key precursor aryl-methanesulfonyl chloride (33) may be prepared either from the reaction of aryl-methylmagnesium chloride (34), obtained from the corresponding benzyl chloride (35) and magnesium, or by oxidation of the aryl-methylthioacetate (36) (prepared from the benzyl bromide (37) with chlorine in presence of trace amount of water [Bagnay and Dransch, Chem. Ber., 93, 784 (1960)]. Alternatively, the aryl-methylthioacetate (36) can be oxidized with sulfuryl chloride in presence of acetic anhydride to form arylmethylsulfinyl chloride [S. Thea and G. Cevasco, Tet. Lett., 28, 5193 (1987)], which can be further oxidized with appropriate oxidizing agents to give the sulfonyl chloride (33). The compound (38) can be obtained by reacting the sulfonyl chloride (33) with appropriate amines. The compound (38) may be obtained by reacting the chloride 33 with ammonia followed by an arylating agent.

SCHEME 5f

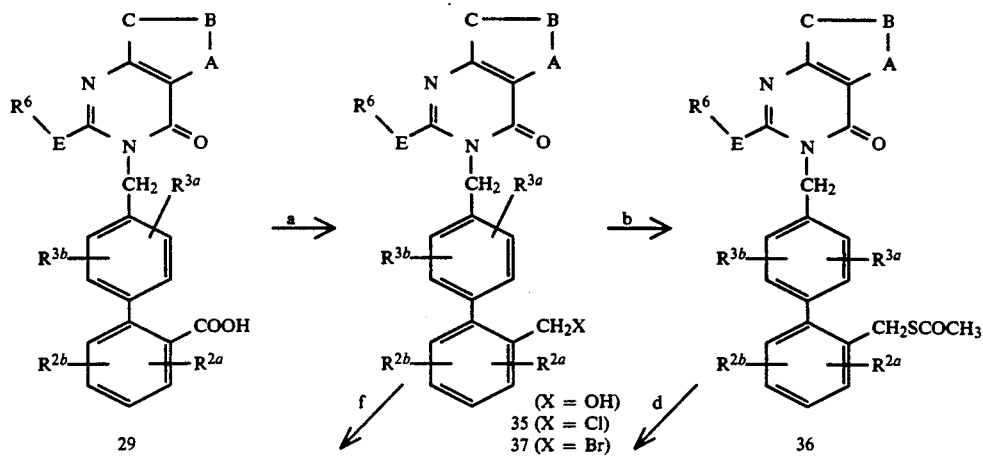

-continued
SCHEME 5f

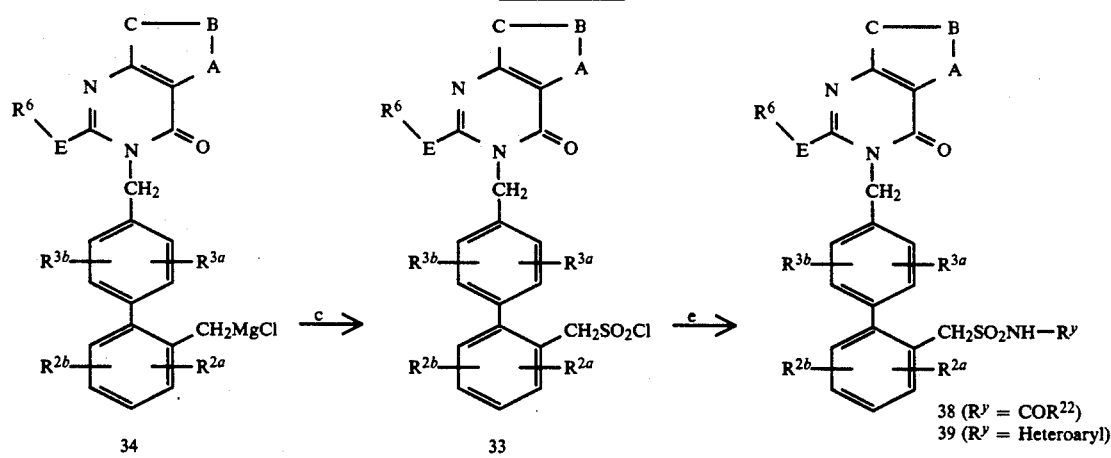

a. (i) EtOCOCl/Et3N, THF, 0° C.
   (ii) NaBH4
   (iii) CCl4 or CBr4/PPh3
b. AcSK
c. SO2Cl2
d. Cl2, AcOH, H2O or,
   (i) SO2Cl2
   (ii) oxidation
e. $R^y$NH2 or,
   (i) NH3
   (ii) Acylation
f. Mg.

Compounds where $R^1$=—NHSO2NHR[22] may be prepared by the reaction of appropriate primary amines with the sulfamide (40) [S. D. McDermott and W. J. Spillane, *Synthesis*, 192 (1983)], as described in Scheme 5g. The compound (40) may be obtained from the corresponding N-t-butylsulfamide (41) after treatment with anhydrous trifluoroacetic acid [J. D. Catt and W. L. Matier, *J. Org. Chem.*, 39, 566 (1974)]. The N-t-butylsulfamide (41) may be prepared by the reaction of the aromatic amine (42) (prepared as in Scheme 5c) with t-butylsulfamoyl chloride [W. L. Matier, W. T. Comer and D. Deitchman, *J. Med. Chem.*, 15, 538 (1972)].

SCHEME 5g

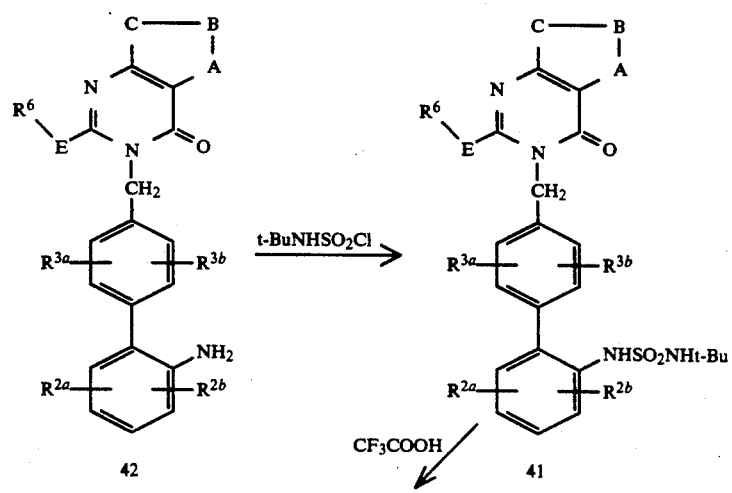

SCHEME 5g

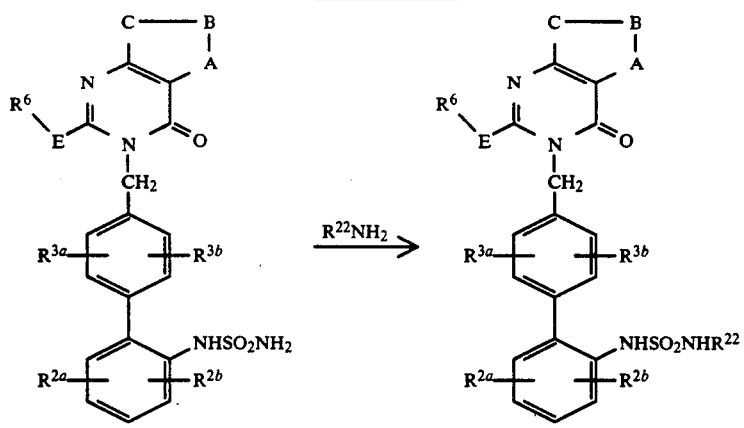

In certain cases due to the nature of the heterocycle being prepared and to the availability of starting materials, it may be advantageous to prepare some of the compounds of this invention from a suitably functionalized pyrimidinone ring and then ring closing to compounds of Formula (I). For example, appropriately functionalized 2-substituted-purine-6(1H)-one's (2) may be synthesised from 4,5-diaminopyrimidin-6(1H)-one's (43) by condensation with acids, amides, orthoesters, acid chlorides and amidines to give, following treatment with base and heat, the desired heterocycles (Scheme 6). (14,15,16) This conversion is known as the Taube reaction. The heterocycle may then be alkylated with (6) as shown in Scheme 2.

SCHEME 6

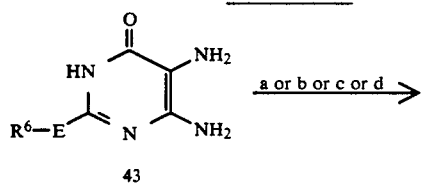

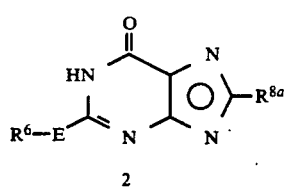

a = $R^{8a}-\overset{O}{\underset{\|}{C}}-Cl$ b = $R^{8a}-C(O(C_1-C_4-alkyl))_3$ c = $R^{8a}-\overset{O}{\underset{\|}{C}}-NH_2$ d = $R^{8a}-\overset{NH_2}{\underset{|}{C}}=NH$ An alternative method of preparing 2,8-disubstituted purin-6(1H)-ones is to condense aminomalonamidamidine (44) with ortho esters to give the heterocycle (45) (Scheme 7)(17). This may then be selectively alkylated as shown in Scheme 2 to give compounds of Formula (I).

SCHEME 7

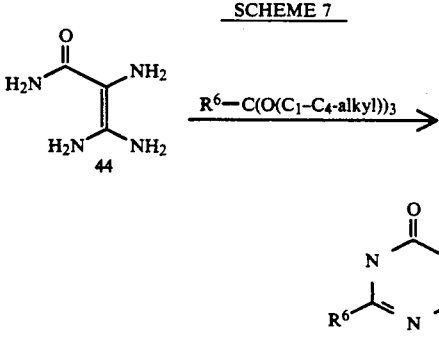

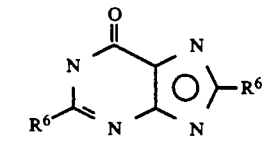

2-Substituted-furo(2,3-d)pyrimidin-4(3H)-ones (46) have been prepared from acid catalysed ring closing of 5-acetonylpyrimidin-4-ones (47)(18). (Scheme 8) The heterocycle (46) may then be alkylated with (6) as shown in Scheme 2 and deprotected as necessary to give compounds of Formula (I).

SCHEME 8

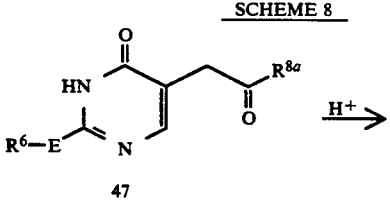

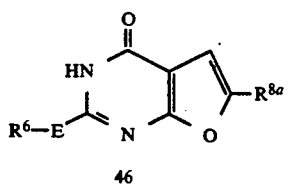

2,3,6-Trisubstituted thieno{2,3-d}pyrimidin-4(3H)-ones (1) have been prepared by heating 2-acylaminothiophene-3-carboxylates (48) with phosphorous pentoxide, N,N'-dimethylcyclohexylamine and an amine hydrochloride at 180° C. (Scheme 9). [19] Deprotection of (48) would give rise to compounds of Formula I.

SCHEME 9

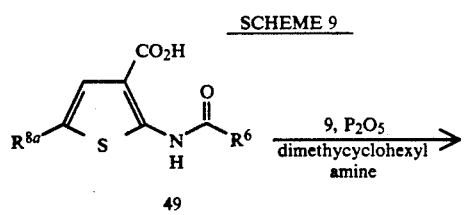

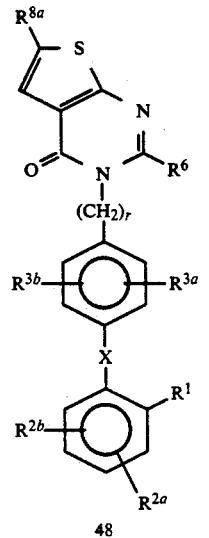

In the cases where E=O,S, a vicinally substituted amino carboxylic acid amide heterocycle (50) may be reacted with phosgene, carbonyldiimidazole, ethyl carbonate, urea, thiourea, carbon disulfide, thiophosgene and other carbonyl and thiocarbonyl equivalents to give heterocycles of structure (51) (Scheme 10). These may, under appropriate conditions, be alkylated on oxygen or sulfur to give compounds of type (52). These may, in turn, be alkylated with (6) as shown in Scheme 2 to give compounds of Formula (I).

Alternatively, (51) may be protected so as to allow conversion of the newly formed carbonyl to iminoyl chloride through the action of a chlorinating agent such as phosphoryl chloride. Reaction of the iminoyl chloride with an amine should give rise to compounds of structure (53) where E=N. These compounds may then be converted to compounds of Formula (I) by appropriate protection and alkylation with (6) as shown in Scheme 2.

SCHEME 10

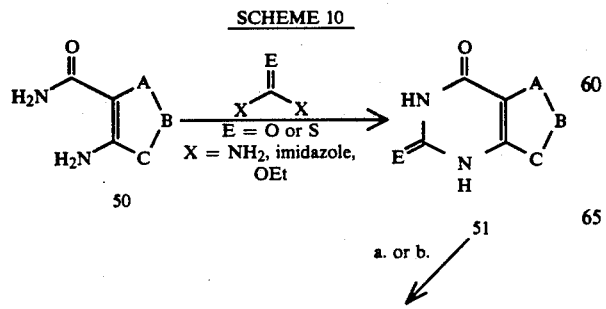

-continued
SCHEME 10

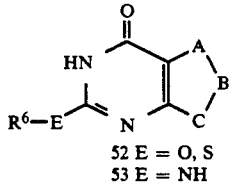

52 E = O, S
53 E = NH a. NaH, $R^6$—halo, DMF
b. i) $POCl_3$ ii) $R^6NH_2$

2-Substituted pyrrolo{3,2-d}pyrimidin-4(3H)-ones may be prepared from enamine (54) by treatment with base to give the pyrrole (55) followed by condensation with an anhydride and treatment with base to give the pyrimidinone (56) (Scheme 11)[20]. This may, in turn, be alkylated, after appropriate protecting groups have been added, with (6) as shown in Scheme 2.

SCHEME 11

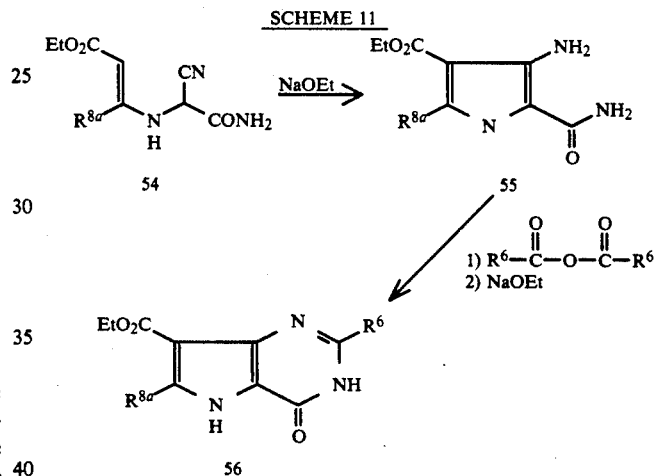

The synthesis of oxazolo{5,4-d}pyrimidin-7(6H)-ones is reported to be precluded from 2-amino-3-cyanooxazoles via acylation and hydrolysis/cyclization with basic hydrogen peroxide due to the instability of the oxazole ring. An alternative route is available from the pyrimidinone (57) by treatment with an alkyl anhydride to give (58) (Scheme 12)[21]. This may, in turn, be alkylated with (6) as indicated in Scheme 2 to give structures of Formula (I).

SCHEME 12

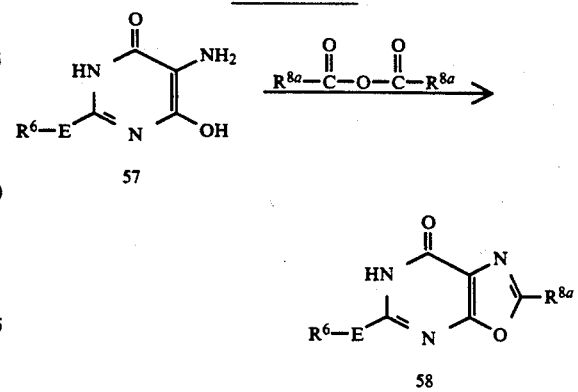

Oxazolo{4,5-d}pyrimidin-7(6H)-ones may be prepared from 2-acylamino-2-cyanoacetamides via intermediate carboxamide hydrochlorides. Thus, 2-acylamino-2-cyano acetamides (59) are converted to oxazoles (60) by treatment with acid. Condensation of the oxazoles (60) with an orthoformate gave 5-unsubstituted oxazolo{4,5-d}pyrimidin-7(6H)-ones (61) (Scheme 13).[22] Condensation with alkyl orthoformates should give rise to the 5-substituted series. Alkylation of (61) will give rise to compounds of Formula (I) as indicated in Scheme 2.

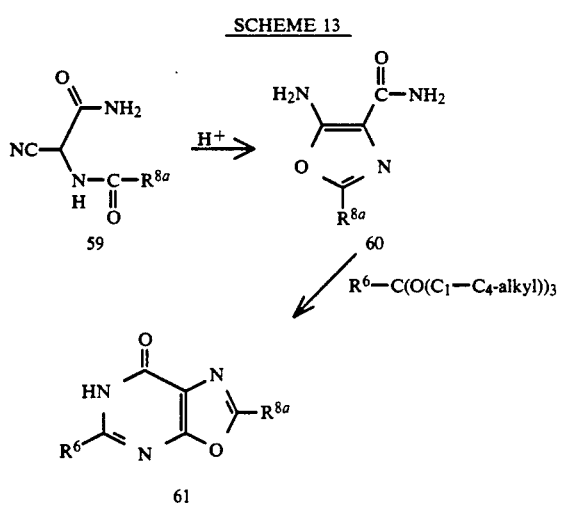

Further functionalization of compounds of Formula (I) where $R^{8a}$ or $R^{8b}$ is nitro is available through the following route (Scheme 14). The nitro group of (62) may be reduced to the amine (63) by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates (64). The carbamate may be isolated and then deprotonated with lithium hexamethyldisilazide and alkylated to give the N,N-dialkylated carbamates (65). Alternatively this process may be carried out in one pot by first preforming the anilinium anion, acylating it and then deprotonating in situ and alkylating with $R^4$ iodide group to give (65). The amine (63) reacts slowly with isocyanates to give ureas (66). Trisubstituted ureas (67) may be prepared from the benzyl carbamate (64) ($R^{22}$=benzyl) by treatment with the magnesium salt of a secondary amine. The trisubstituted ureas may be N-alkylated by deprotonation with lithium hexamethyldisilazide and alkylation with an $R^4$ iodide to give (68). The amine may be further derivatized or converted to other groups by means of chemical procedures well known to those skilled in the art.

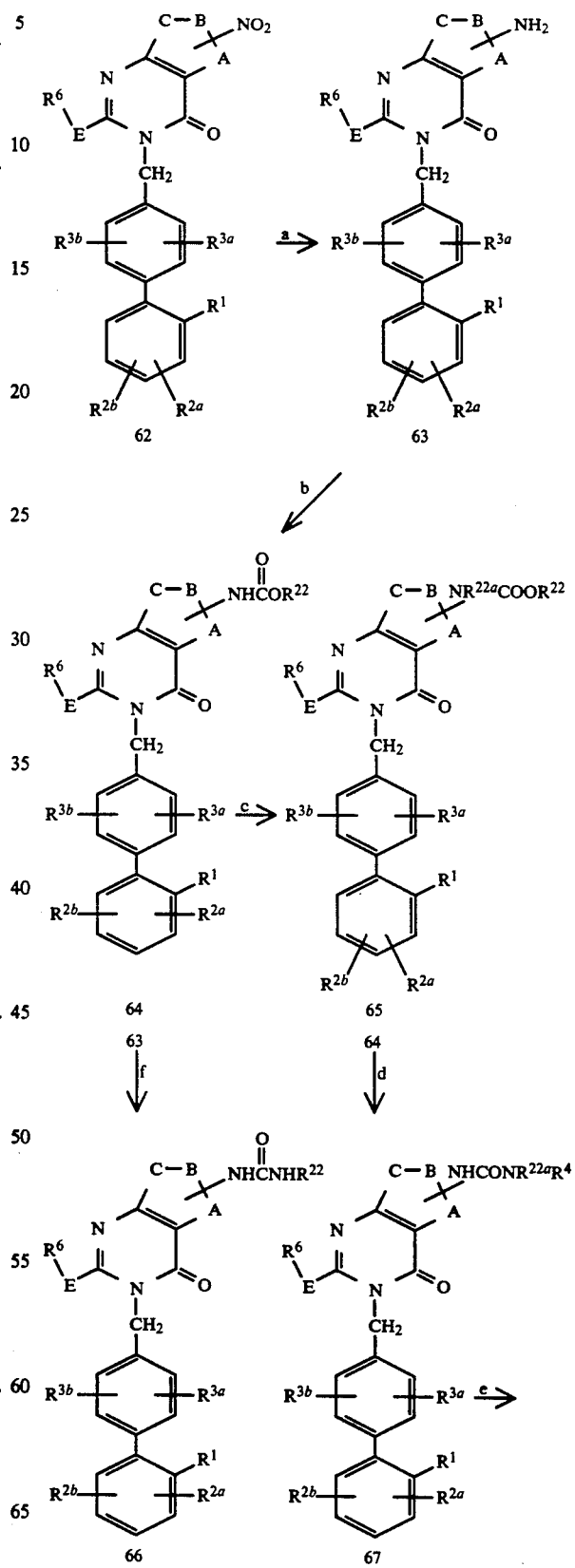

-continued
SCHEME 14

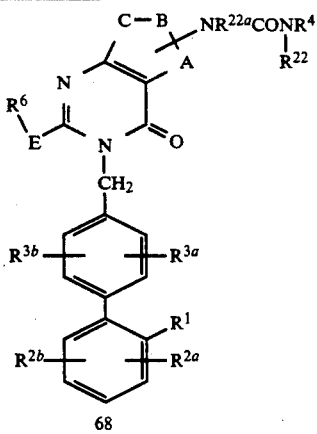

68 a. H₂, 10% Pd/C, EtAc
b. NaH, ClCOR²², DMF
c. LiN(TMS)₂, R²²ᵃI
d. MeMgBr, R⁴NHR²², THF, reflux
e. LiN(TMS)₂, R²²ᵃI, DMF
f. R²²NCO, CH₂Cl₂

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methane-sulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl₂ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added ¹²⁵I-Sar¹Ile⁸-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC₅₀) of potential AII antagonist which gives 50% displacement of the total specifically bound ¹²⁵I-Sar¹Ile⁸-angiotensin II was presented as a measure of the efficacy of such compounds as AII antagonists.

Receptor Assay Using Bovine Adrenal Cortex Preparation

Bovine adrenal cortex was selected as the source of AII receptor. Weighted tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na₂HPO₄ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC₅₀) of potential AII antagonist which gives 50% displacement of the total specifically bound ³H-angiotensin II was presented as a measure of the efficacy of such compounds as AII antagonists.

Receptor Assay Using Rat Brain Membrane Preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM Na₂.EDTA, 10 mM Na₂HPO₄ (pH 7.4) and 0.1 mM PMSF by resuspension and centrifugation. For binding assays, the pellets were resuspended in 160 volumes of binding assay buffer (100 mM NaCl, 10 mM Na₂HPO₄, 5 mM Na₂.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For ¹²⁵I.Ile⁸-angiotensin II binding assays, 10 μl of solvent (for total binding), Sar¹,Ile⁸- angiotensin II (1 μM) (for nonspecific binding) or test compounds (for displacement) and 10 μl of [$^{125}$I]Sar$^1$-,Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Using the methodology described above, representative compounds of the invention were evaluated and were found to exhibit an activity of at least $IC_{50} < 50$ μM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later, antagonists of formula (I) were administered intravenously or orally. Angiotensin II was then typically given at 5, 10, 15, 30, 45 and 60 minute intervals and every half hour thereafter for as long as the test compound showed activity. The change in the mean arterial blood pressure was recorded for each angiotensin II challenge and the percent inhibition of angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy, and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated introcular pressure and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosage that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *Rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitredipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

All $^1$H-NMR spectra were recorded on a Varian XL-400 Fourier transform spectrometer unless otherwise noted. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of dry nitrogen under standard conditions for those skilled in the art.

EXAMPLES 2-n-Butyl-5-methyl-thieno{2,3-d}pyrimidin-4(3H)-one

To a solution of 3.7 g (0.2 mol) of ethyl 2-amino-4-methylthiophene-3-carboxylate in 30 ml dry dioxane was added 1.82 g (0.022 mol) of valeronitrile. The solution was treated with dry HCl gas over a period of 5 hours. The mixture was poured into 200 ml of ice water and made basic with 10% $NH_4OH$. The resulting solids were collected by filtration. A solution of the residue in MeOH was allowed to stand over 3 days and gave rise to a mass of crystals that were shown to be starting material. The filtrate was concentrated in vacuo and the residue was triturated with 20% EtOAc/hexanes. A white precipitate formed that was removed by filtration to give the desired heterocycle. $^1$H-NMR ($CDCl_3$-200 MHz): 0.97 (t, 3H, J=7.3 Hz), 1.49 (m, 2H), 1.70–1.91 (m, 3H), 2.58 (s, 3H), 2.76 (3 line m, 2H, J=8.2 Hz), 6.77 (bs, 1H).

2-n-Butyl-thieno{3,2-d}pyrimidin-4(3H)-one

To a solution of 3.14 g (0.02 mol) of methyl 3-aminothiophene-2-carboxylate in 30 ml of dioxane was added 1.83 g (0.022 mol) of valeronitrile. Dry HCl was added over a period of 5 hours and the reaction mixture was then heated to 70° C. for 3 hours. The mixture was allowed to stand overnight at room temperature. The reaction mixture was diluted with 200 ml of ice water, made basic by addition of $NH_4OH$ and after standing for 30 minutes was filtered, and the filtrate concentrated in vacuo. The residue was purified by flash chromatography eluting with 50% EtOAc/hexanes after applying a suspension of the product in $CH_2Cl_2$ to the column. $^1$H-NMR ($CDCl_3$): 0.96 (t, 3H, J=7.4 Hz), 1.44 (m, 2H), 1.62 (bs, 1H), 1.82 (m, 2H), 2.79 (3 line m, 2H, J=7.8 Hz), 7.33 (d, 1H, J=5.3 Hz), 7.81 (d, 1H, J=5.3 Hz).

2-Butyl-4,5,6,7-tetrahydrobenzo[b]thieno{2,3-d}pyrimidin-4(3H)-one

To a solution of 5 g (0.022 mol) of ethyl 2-amino-4,5,6,7-tetrahydrobenzothiophene-3-carboxylate and 2.6 ml (0.024 mol) of valeronitrile in 75 ml of dry dioxane was added HCl gas via a gas dispersion tube. A precipitate formed that gradually redissolved. After 5.5 hours of gas addition, the solution was heated to 70° C. for 3 hours. The reaction mixture was cooled to room temperature and stirred overnight. The mixture was poured into 300 ml of ice water and the solid residue was removed by filtration. The residue was recrystalized from MeOH to give colorless crystals of the desired product. $^1$H-NMR ($CDCl_3$): 0.93 (t, 3H, J=7.4 Hz), 1.41 (m, 2H), 1.83 (m, 6H), 2.75 (M, 4H), 2.98 (3 line m, 2H, J=5.81 Hz), 12.38 (bs, 1H).

GENERAL METHOD FOR ALKYLATING HETEROCYCLE WITH BIPHENYL BROMIDE

To a suspension of 1 mmol of NaH in 1 ml of dry DMF at 0° C. was added the pyrimidinone as a solid under nitrogen gas. The solution was stirred for 30 minutes at which time a solution of 1.1 mmol of N-triphenylmethyl-5-[2-(4'-bromomethylbiphenyl)]tetrazole in 1.75 ml of dry DMF. The reaction mixture was stirred at room temperature overnight, diluted with 25 ml of EtOAc and washed with water (3×5 ml) and brine (1×10 ml) and dried over MgSO$_4$. The mixture was filtered and the filtrate was concentrated in vacuo. The residue was purified by flash chromatography over silica gel eluting with an appropriate mixture of EtOac/hexanes to give the product in approximately 50% yield.

GENERAL PROCEDURE FOR THE DEPROTECTION OF THE TETRAZOLE

The triphenyl methyl group was removed by dissolving, for example, the pyrimidinone (0.2 g) in MeOH (5 ml) in the presence of several drops (3-5) of concentrated hydrochloric acid. After 2 hours at room temperature a few crystals of phenophthalein were added and the reaction mixture made basic by addition of 5N NaOH solution. The reaction mixture was reacidified by addition of acetic acid and then concentrated in vacuo. The residue was dissolved in 20 ml of EtOAc and washed with water (3×5 ml) and brine (1×5 ml) and dried over MgSO$_4$. The mixture was filtered and concentrated in vacuo and the residue was purified by flash chromatography over silica gel eluting with the solvent indicated in the descriptions below. The compounds were characterized by $^1$H-NMR and Fast Atom Bombardment Mass Spectroscopy (FABMS).

The following compounds were prepared by the general methods described immediately hereinabove:

2-n-Butyl-5-methyl-3-[(2'-tetrazol-5-yl)-biphen-4-yl)-methyl]-thieno{2,3-d}pyrimidin-4(3H)-one The product was eluted with 40% EtOAc/hexanes 1% Acetic acid. $^1$H-NMR-(CDCl$_3$): 0.87 (t, 3H, J=7.4 Hz), 1.36 (m, 2H), 1.69 (m, 2H), 2.38 (s, 3H), 2.70 (3 line m, 2H, J=8.0 Hz), 5.25 (bs, 2H), 6.73 (s, 1H), 6.97 and 7.03 (ABq, 4H, J=8.02 Hz), 7.13 (m, 1H), 7.35 (d, 1H, J=6.7 Hz), 7.46 (t, 1H, J=6.6 Hz), 7.55 (t, 1H, J=7.3 Hz), 7.86 (d, 1H, J=7.3 Hz).

2-n-Butyl-3-[(2'-tetrazol-5-yl)-biphen-4-yl)-methyl]-thieno{3,2-d}pyrimidin-4(3H)-one The product was eluted with 50% EtOAc/hexanes 1% Acetic acid. $^1$H-NMR-(CDCl$_3$): 0.91 (t, 3H, J=7.4 Hz), 1.40 (m, 2H), 1.74 (m, 2H), 2.76 (3 line m, 2H, J=7.8 Hz), 5.41 (bs, 2H), 7.17 (s, 4H), 7.26 (d, 1H, J=5.2 Hz), 7.55 (m, 2H), 7.38 (dd, 1H, J=1.3, 7.4 Hz), 7.76 (d, 1H, J=5.2 Hz), 8.10 (d, 1H, J=7.6 Hz).

2-Butyl-3-[(2'-tetrazol-5-yl)-biphen-4-yl)-methyl]-4,5,6,7-tetrahydrobenzo[b]thieno{2,3-d}pyrimidin-4(3H)-one The product was purified by trituration from hexanes/EtOAc. $^1$H-NMR-(CDCl$_3$): 0.89 (t, 3H, J=7.0 Hz), 1.38 (m, 2H), 1.68-1.87 (m, 6H), 2.72 (3 line m, 4H, J=8.7 Hz), 2.85 (3 line m, 2H, J=4.3 Hz), 5.29 (bs, 2H), 7.07 and 7.12 (ABq, 4H, J=8.1 Hz), 7.37 (d, 1H, J=8.1 Hz), 7.51 (m, 2H), 8.02 (d, 1H, J=7.5 Hz). FABMS: 497 (M++1).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-n-butyl-5-methyl-3-[(2'-tetrazol-5-yl)-biphen-4-yl)-methyl]-thieno{2,3-d}-pyrimidin-4(3H)-one | 50 |
| Lactose | 149 |
| Magnesium stearate | 1 |
| Capsule (size No. 1) | 200 |

2-n-Butyl-5-methyl-3-[(2'-tetrazol-5-yl)biphen-4-yl)-methyl]-thieno{2,3-d}pyrimidin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-n-butyl-5-methyl-3-[(2'-tetrazol-5-yl)-biphen-4-yl)-methyl]-thieno{2,3-d}pyrimidin-4(3H)-one (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of 2-n-butyl-5-methyl-3-[(2'-tetrazol-5-yl)-biphen-4-yl)-methyl]-thieno{2,3-d}pyrimidin-4(3H)-one (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 2-n-butyl-5-methyl-3-[(2'-tetrazol-5-yl)-biphen-4-yl)-methyl]-thieno{2,3-d}pyrimidin-4(3H)-one (1-25 mg), butylated hydroxyanisole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-n-butyl-5-methyl-3-[(2'-tetrazol-5-yl)biphen-4-yl)-methyl]-thieno-{2,3-d}pyrimidin-4(3H)-one (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of the Formula (I)

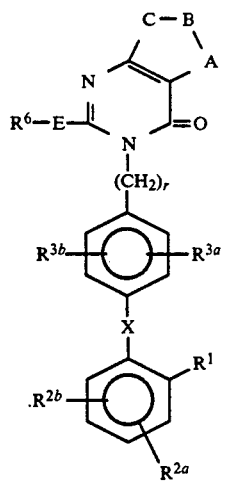
wherein:
A-B-C together with the pyrimidinone to which it is attached form a member selected from the group:
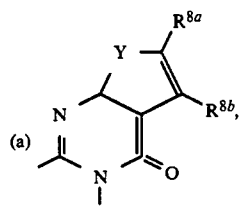
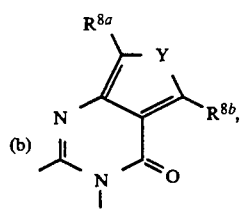
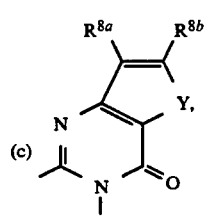
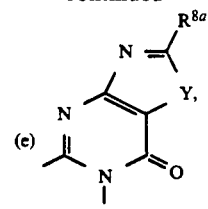
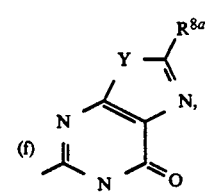
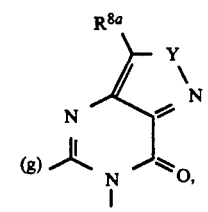
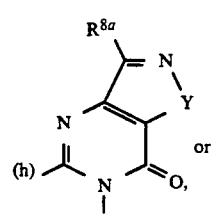
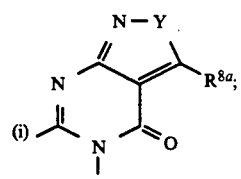
Y is O, S or NR$^7$;
R$^1$ is
(a) —CO$_2$R$^4$,
(b) —SO$_3$R$^5$,
(c) —NHSO$_2$R$^{22}$,
(d) —PO(OR$^5$)$_2$,
(e) —SO$_2$—NH—R$^{22}$,
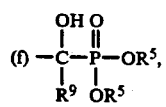
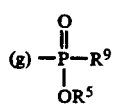
(h) —CH$_2$SO$_2$NH—R$^{22}$,
(i) —SO$_2$NH—CO—R$^{22}$,
(j) —CH$_2$SO$_2$NH—CO—R$^{22}$,
(k) —CONH—SO$_2$R$^{22}$, (l) —CH$_2$CONH—SO$_2$R$^{22}$,
(m) —NHSO$_2$NHCO—R$^{22}$,
(n) —NHCONHSO$_2$—R$^{22}$,

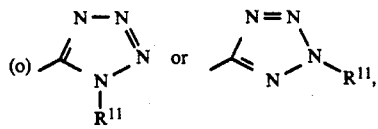

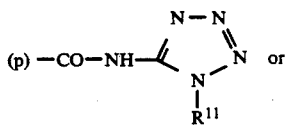

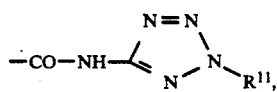

(q) —CONHNHSO$_2$CF$_3$,
(r) —SO$_2$NH—CN,

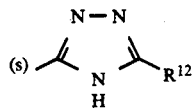

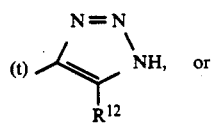

(u) —SO$_2$NHCONR$^4$R$^{22}$, wherein
heteroaryl is an unsubstituted, monosubstituted or disubstituted five or six membered aromatic ring which contains from 1 to 3 heteroatoms selected from the group consisting of O, N or S and wherein the substituents are members selected from the group consisting of —OH, —SH, —C$_1$-C$_4$-alkyl, —C$_1$-C$_4$-alkoxy, —CF$_3$, Cl, Br, F, I, —NO$_2$, —CO$_2$H, —CO$_2$—(C$_1$-C$_4$-alkyl), —NH$_2$, —NH(-C$_1$-C$_4$-alkyl) and —N(C$_1$-C$_4$-alkyl)$_2$;

R$^{2a}$ and R$^{2b}$ are each independently
(a) H,
(b) Cl, Br, I, or F,
(c) NO$_2$,
(d) NH$_2$,
(e) C$_1$-C$_4$-alkylamino,
(f) di(C$_1$-C$_4$-alkyl)amino,
(g) SO$_2$NHR$^9$,
(h) CF$_3$,
(i) C$_1$-C$_6$-alkyl,
(j) C$_1$-C$_6$-alkoxy,
(k) C$_1$-C$_6$-alkyl-S—,
(l) C$_2$-C$_6$-alkenyl,
(m) C$_2$-C$_6$-alkynyl,
(n) aryl,
(o) aryl(C$_1$-C$_4$-alkyl), or
(p) C$_3$-C$_7$-cycloalkyl;

R$^{3a}$ is
(a) H,
(b) Cl, Br, I, or F,
(c) C$_1$-C$_6$-alkyl,
(d) C$_1$-C$_6$-alkoxy, or
(e) C$_1$-C$_6$-alkoxyalkyl;

R$^{3b}$ is
(a) H,
(b) Cl, Br, I, or F,
(c) NO$_2$,
(d) C$_1$-C$_6$-alkyl,
(e) C$_1$-C$_6$-acyloxy,
(f) C$_3$-C$_7$-cycloalkyl,
(g) C$_1$-C$_6$-alkoxy,
(h) —NHSO$_2$R$^4$,
(i) hydroxy(C$_1$-C$_4$-alkyl),
(j) aryl(C$_1$-C$_4$-alkyl),
(k) C$_1$-C$_4$-alkylthio,
(l) C$_1$-C$_4$-alkyl sulfinyl,
(m) C$_1$-C$_4$-alkyl sulfonyl,
(n) NH$_2$,
(o) C$_1$-C$_4$-alkylamino,
(p) di(C$_1$-C$_4$-alkyl)amino,
(q) fluoro-C$_1$-C$_4$-alkyl-,
(r) —SO$_2$—NHR$^9$,
(s) aryl,
(t) furyl,
(u) CF$_3$,
(v) C$_2$-C$_6$-alkenyl, or
(w) C$_2$-C$_6$-alkynyl;

wherein
aryl is phenyl or naphthyl or substituted phenyl or naphthyl with one or two substituents selected from the group consisting of Cl, Br, I, F, N(R$^4$)$_2$, CO$_2$R$^4$, C$_1$-C$_4$-alkyl, C$_1$-C$_4$-alkoxy, NO$_2$, CF$_3$, C$_1$-C$_4$-alkylthio, or OH;

R$^4$ is H, aryl, C$_1$-C$_6$ alkyl, or substituted C$_1$-C$_6$ alkyl with an aryl or heteroaryl substituent;

R$^{4a}$ is aryl, C$_1$-C$_6$ alkyl, or substituted C$_1$-C$_6$ alkyl with an aryl substituent;

R$^5$ is H,

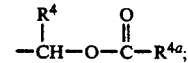

E is a single bond, —NR$^{13}$(CH$_2$)$_s$—, —S(O)$_x$(CH$_2$-)$_s$— where x is 0 to 2 and s is 0 to 5, —CH(OH)—, —O—, CO—;

R$^6$ is
(a) aryl or substituted aryl with 1 or 2 substituents selected from the group consisting of Cl, Br, I, F, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, C$_3$-C$_7$-cycloalkyl, or C$_3$-C$_{10}$-alkenyl,
(b) C$_1$-C$_6$-alkyl, C$_2$-C$_5$-alkenyl or C$_2$-C$_5$-alkynyl or substituted C$_1$-C$_6$-alkyl, C$_2$-C$_5$-alkenyl or C$_2$-C$_5$-alkynyl substituted with a substituent selected from the group consisting of aryl, C$_3$-C$_7$-cycloalkyl, Cl, Br, I, F, CF$_3$, CF$_2$CF$_3$, —NH$_2$, —NH(C$_1$-C$_4$-alkyl), —OR$^4$ —N(C$_1$-C$_4$-alkyl)$_2$, —NH—SO$_2$R$^4$, —COOR$^4$, or —SO$_2$NHR$^9$,
(c) an unsubstituted, monosubstituted or disubstituted heteroaromatic 5 or 6 membered cyclic ring which contains one to three members selected from the group consisting of N, O, S, and wherein the substituents are members selected from the group consisting of —OH, —SH, C$_1$-C$_4$-alkyl, C$_1$-C$_4$-alkoxy, —CF$_3$, Cl, Br, I, F, or NO$_2$,
(d) C$_3$-C$_7$-cycloalkyl,
(e) perfluoro-C$_1$-C$_4$-alkyl, or (f) H;

R⁷ is:
(a) H,
(b) $C_1-C_6$-alkyl, $C_2-C_6$-alkenyl or $C_2-C_6$-alkynyl or substituted $C_1-C_6$-alkyl, $C_2-C_6$-alkenyl or $C_2-C_6$-alkynyl substituted with a substituent selected from the group consisting of $C_3-C_7$-cycloalkyl, Cl, Br, I, F, —OH, —NH₂, —NH(-$C_1-C_4$-alkyl), —N($C_1-C_4$ alkyl)₂, —NHSO₂R⁴, —COOR⁴, $C_1-C_4$-alkoxyl, $C_1-C_4$-alkylthio, —CONH₂, —COR⁴, or —SO₂R⁴, —NR⁴COR²², —NR⁴CO₂R²², —NR⁴CONR⁴R²², or —CO heteroaryl,
(c) —COR⁴,
(d) aryl, or substituted aryl wherein the substitutents are V or W,
(e) aryl-$C_1-C_6$-alkyl in which the aryl group is unsubstituted, mono- or disubstituted with V or W,
(f) —OR⁴,
(g) heteroaryl, or
(h) —CON(R⁴)₂;

V and W are independently:
(a) H,
(b) $C_1-C_5$-alkoxy,
(c) $C_1-C_5$-alkyl,
(d) hydroxy,
(e) $C_1-C_5$-alkyl-S(O)$_x$—,
(f) CN,
(g) NO₂,
(h) N(R⁴)₂,
(i) CON(R⁴)₂,
(j) CO₂R⁴,
(k) COR⁴,
(l) CF₃,
(m) Cl, Br, I, or F,
(n) hydroxy-$C_1-C_5$-alkyl,
(o) $C_1-C_5$-alkylthio,
(p) —SO₂NR⁹R¹⁰,
(q) $C_3-C_7$-cycloalkyl, or
(r) $C_2-C_{10}$-alkenyl;

R⁸ᵃ and R⁸ᵇ are independently
(a) H,
(b) $C_1-C_8$-alkyl, $C_2-C_6$-alkenyl or $C_2-C_6$-alkynyl or substituted $C_1-C_8$-alkyl, $C_2-C_6$-alkenyl or $C_2-C_6$-alkynyl with a substituent selected from the group consisting of —OH, -guanidino, $C_1-C_4$-alkoxy, —N(R⁴)₂, COOR⁴, —CON(R⁴)₂, —O—COR⁴, -aryl, -heteroaryl, —S(O)$_x$-R²², -tetrazol-5-yl, —CONHSO₂R²², —SO₂NH-heteroaryl, —SO₂NHCOR²², —PO(OR⁴)₂, —PO(OR⁴)R⁹, —SO₂NH—CN, —NR¹⁰COOR²², —(CH₂)₁₋₄R⁴, Cl, Br, F, or I,
(c) —CO-aryl,
(d) —$C_3-C_7$-cycloalkyl,
(e) Cl, Br, I, or F,
(f) —OH,
(g) —OR²²,
(h) —$C_1-C_4$-perfluoroalkyl,
(i) —S(O)$_x$—R²²,
(j) —COOR⁴,
(k) —SO₃H,
(l) —NR²²ᵃR²²,
(m) —NR⁴COR²²,
(n) —NR⁴COOR²²,
(o) —SO₂NR⁴R⁹,
(p) —NO₂,
(q) —N(R²²ᵃ)SO₂R²²,
(r) —NR²²ᵃCONR⁴R²²,

(s) —OCNR²²R⁹, (t) -aryl or -heteroaryl,
(u) —SO₂NH-heteroaryl,
(v) —SO₂NHCOR²²,
(w) —CONHSO₂R²²,
(x) —PO(OR⁴)₂,
(y) —PO(OR⁴)R⁴,
(z) -tetrazol-5-yl,
(aa) —CONH(tetrazol-5-yl),
(bb) —COR⁴,
(cc) —SO₂NHCN
(dd) —NR⁴SO₂NR⁴R²²,
(ee) —NR⁴SO₂OR²²,
(ff) —CONR⁴R²²,

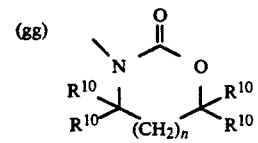

where n=0 or 1, or

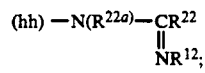

R⁹ is H, $C_1-C_5$-alkyl, aryl or arylmethyl;
R¹⁰ is H, $C_1-C_4$-alkyl;
R¹¹ is H, $C_1-C_6$-alkyl, $C_1-C_4$-alkenyl, $C_1-C_4$-alkoxy alkyl, or

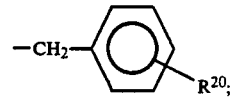

R¹² is —CN, —NO₂, —CF₃ or —CO₂R⁴;
R¹³ is H, ($C_1-C_4$-alkyl)CO—, $C_1-C_6$-alkyl, allyl, $C_3-C_6$-cycloalkyl, aryl or arylmethyl;
R¹⁴ is H, $C_1-C_8$-alkyl, $C_1-C_8$-perfluoroalkyl, $C_3-C_6$-cycloalkyl, aryl or arylmethyl;
R¹⁵ is H, $C_1-C_6$-alkyl;
R¹⁶ is H, $C_1-C_6$-alkyl, $C_3-C_6$-cycloalkyl, aryl or arylmethyl;
R¹⁷ is —NR⁹R¹⁰, —OR¹⁰, —NHCONH₂, —NHCSNH₂,

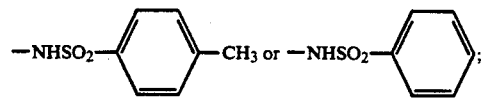

R¹⁸ and R¹⁹ are independently $C_1-C_4$-alkyl or taken together are —(CH₂)$_q$— where q is 2 or 3;
R²⁰ is H, —NO₂, —NH₂, —OH or —OCH₃;
R²¹ is
(a) aryl,
(b) heteroaryl, or
(c) $C_1-C_4$-alkyl or substituted $C_1-C_4$-alkyl with a substituent selected from the group consisting of aryl, heteroaryl as defined above, —OH, —NH₂, —NH($C_1$-$C_4$-alkyl),  —N($C_1$-$C_4$-alkyl)$_2$, —CO$_2$R$^{4a}$, Cl, Br, F, I, or —CF$_3$;

$R^{22}$ is
(a) aryl,
(b) heteroaryl,
(c) $C_3$-$C_7$-cycloalkyl,
(d) $C_1$-$C_6$-alkyl or substituted $C_1$-$C_6$-alkyl with a substituent selected from the group consisting of aryl, heteroaryl, —OH, —SH, $C_1$-$C_4$-alkyl, —O($C_1$-$C_4$-alkyl), —S($C_1$-$C_4$-alkyl), —CF$_3$, Cl, Br, F, I, —NO$_2$, —CO$_2$H, CO$_2$—($C_1$-$C_4$-alkyl), —NH$_2$, —NH($C_1$-$C_4$-alkyl), —N($C_1$-$C_4$-alkyl)$_2$, —PO$_3$H$_2$, —PO(OH)(O—$C_1$-$C_4$-alkyl), —PO(OR$^4$)R$^9$, morpholinyl or N—$C_1$-$C_4$ alkyl piperazinyl, or
(e) perfluoro-$C_1$-$C_4$-alkyl;

$R^{22a}$ is
(a) hydrogen,
(b) aryl,
(c) heteroaryl,
(d) $C_3$-$C_7$-cycloalkyl,
(e) $C_1$-$C_6$-alkyl or substituted $C_1$-$C_6$-alkyl with a substituent selected from the group consisting of aryl, heteroaryl, —OH, —SH, $C_1$-$C_4$-alkyl, —O($C_1$-$C_4$-alkyl), —S($C_1$-$C_4$-alkyl), —CF$_3$, Cl, Br, F, I, —NO$_2$, —CO$_2$H, CO$_2$—($C_1$-$C_4$-alkyl), —NH$_2$, —NH($C_1$-$C_4$-alkyl), —N($C_1$-$C_4$-alkyl)$_2$, —PO$_3$H$_2$, —PO(OH)(O—$C_1$-$C_4$-alkyl), —PO(OR$^4$)R$^9$, morpholinyl or N—($C_1$-$C_4$-alkyl)-piperazinyl, or
(f) perfluoro-$C_1$-$C_4$-alkyl;

X is
(a) a carbon-carbon single bond,
(b) —CO—,
(c) —O—,
(d) —S—, (e) —N—,
    |
    R$^{13}$ (f) —CON—,
    |
    R$^{15}$ (g) —NCO—,
    |
    R$^{15}$ (h) —OCH$_2$—,
(i) —CH$_2$O—
(j) —SCH$_2$—,
(k) —CH$_2$S—,
(l) —NHC(R$^9$)(R$^{10}$),
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—, (v) 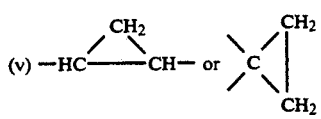

-continued (w) 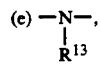

(x) 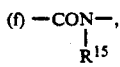

(y) 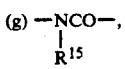

(z) 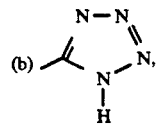

r is 1 or 2; and a pharmaceutically acceptable salt thereof.

2. A compound of claim 1 wherein:
$R^1$ is
(a) —CO$_2$R$^4$, (b) 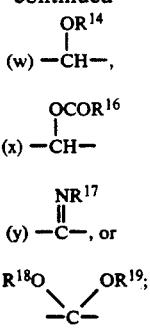

(c) —NH—SO$_2$R$^{22}$,
(d) —SO$_2$NH—heteroaryl,
(e) —CH$_2$SO$_2$NH—heteroaryl,
(f) —SO$_2$NH—CO—R$^{22}$,
(g) —CH$_2$SO$_2$NH—CO—R$^{22}$,
(h) —CONH—SO$_2$R$^{22}$,
(i) —CH$_2$CONH—SO$_2$R$^{22}$,
(j) —NHSO$_2$NHCO—R$^{22}$, or
(k) —NHCONHSO$_2$—R$^{22}$;

$R^{2a}$ is H;
$R^{2b}$ is H, F, Cl, CF$_3$, $C_1$-$C_6$-alkyl, $C_2$-$C_6$-alkenyl, $C_2$-$C_6$-alkynyl, or aryl;
$R^{3a}$ is H;
$R^{3b}$ is H, F, Cl, CF$_3$, $C_1$-$C_4$-alkyl, $C_2$-$C_4$-alkenyl, $C_2$-$C_4$-alkynyl, $C_5$-$C_6$-cycloalkyl, —COOCH$_3$, —COOC$_2$H$_5$, —SO$_2$—CH$_3$, NH$_2$, —N($C_1$-$C_4$-alkyl)$_2$ or —NH—SO$_2$CH$_3$;
E is a single bond, —O— or —S—;
$R^6$ is
(a) $C_1$-$C_5$ alkyl or substituted $C_1$-$C_5$ alkyl with a substituent selected from the group consisting of $C_3$-$C_5$-cycloalkyl, Cl, CF$_3$, CCl$_3$, —O—CH$_3$, —OC$_2$H$_5$, —S—CH$_3$, —S—C$_2$H$_5$, phenyl, or F,
(b) $C_2$-$C_5$-alkenyl or $C_2$-$C_5$-alkynyl, or,
(c) $C_3$-$C_5$-cycloalkyl;
$R^7$ is
(a) H;
(b) $C_1$-$C_6$-alkyl or substituted $C_1$-$C_6$-alkyl with a —OH, —N(R$^4$)$_2$, —NR$^4$COR$^{22}$ —NR$^4$CO$_2$R$^{22}$, or —NR$^4$CONR$^4$R$^{22}$ substituent; or
(c) aryl or substituted aryl with a Cl, —F, —O(C$_1$-$C_4$-alkyl), —CO$_2$R$^4$, or —SO$_2$R$^4$ substituent;
$R^{8a}$ and $R^{8b}$ are independently
(a) H,
(b) $C_1$-$C_8$-alkyl or substituted $C_1$-$C_8$-alkyl with COOR, OCOR$^{4a}$, OH, aryl, or —(CH$_2$)$_{1-4}$R$^4$ substituent,
(c) OR$^{22}$,
(d) —OH,
(e) —NO$_2$,
(f) —N(R$^{22a}$)COR$^{22}$, (g) —CONR⁴R²²,
(h) —N(R²²ᵃ)CO₂R²²,
(i) —NR⁴R²²,
(j) Cl, F, or Br,
(k) —CF₃,
(l) —CO₂R⁴ᵃ,
(m) —CO-aryl,
(n) —S(O)$_x$—R²²,
(o) —SO₂—NR⁴R⁹,
(p) —N(R²²ᵃ)SO₂R²²,
(q) aryl,
(r) —NR²²ᵃCONR⁴R²², or
(s) —N(R²²ᵃ)SO₂N(R⁴)R²²;

X is a single bond; and
r is one.

3. A compound of claim 2 wherein:
A-B-C together with the pyrimidinone to which it is attached form a member selected from the group:

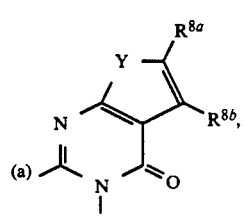

(a)

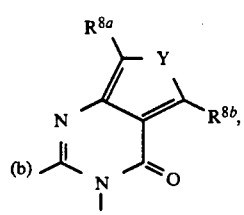

(b)

or

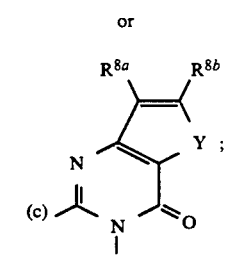

(c)

Y is O, S or NR⁷;
E is a single bond;
R²ᵇ and R³ᵇ are H;
R⁶ is C₁–C₄ alkyl, C₂–C₅ alkenyl, cyclopropyl, —CH₂CH₂CF₃, —CH₂CH₂CH₂CF₃ or cyclopropylmethyl; and
R⁸ᵃ and R⁸ᵇ are each independently H, —C₁–C₄alkyl, —NO₂, —NR⁴R²², —OCH₃, —NR²²ᵃCOOR²², —Cl, CH₂COOR⁴ᵃ, —S(O)$_x$—R²², —NR²²ᵃCONR⁴R²², —CH₂OCO(C₁–C₄-alkyl), —NR²²ᵃCOR²², —CO₂R⁴ᵃ, —F, —CH₂Ph, or —CONR⁴R²².

4. A compound of claim 3 which is a member of the group consisting of:
(1) 2-n-Butyl-5-methyl-3-[(2'-tetrazol-5-yl)biphen-4-yl)-methyl]-thieno{2,3-d}pyrimidin-4(3H)-one;
(2) 2-n-Butyl-3-[(2'-tetrazol-5-yl)-biphen-4yl)-methyl]-thieno{3,2-d}pyrimidin-4(3H)-one; and
(3) 2-Butyl-3-[(2'-tetrazol-5-yl)-biphen-4-yl)-methyl]-4,5,6,7-tetrahydrobenzo[b]thieno{2,3-d}pyrimidin-4(3H)-one.

5. A compound of claim 2 wherein:
A-B-C together with the pyrimidinone to which it is attached form a member selected from the groups:

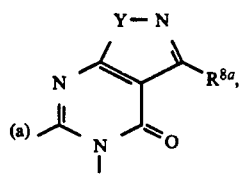

(a)

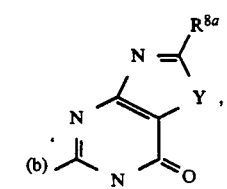

(b)

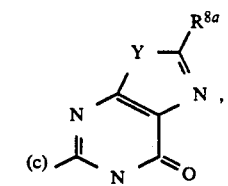

(c)

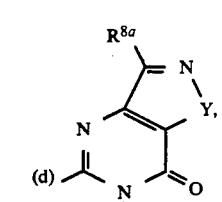

(d)

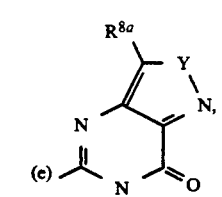

(e)

or

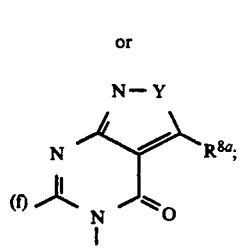

(f)

Y is O, S or NR⁷;
R²ᵃ, R²ᵇ, R³ᵃ and R³ᵇ independently are:
(a) hydrogen,
(b) C₁–C₆alkyl, (c) $C_2$-$C_6$alkenyl,
(d) $C_2$-$C_6$alkynyl,
(e) Cl,
(f) F,
(g) $NO_2$, or
(h) $CF_3$;

$R^6$ is $C_1$-$C_4$alkyl, $C_2$-$C_8$alkenyl, cyclopropyl, —$CH_2CH_2CF_3$, —$CH_2CH_2CH_2CF_3$ or cyclopropylmethyl;

$R^7$ is H or $C_1$-$C_4$alkyl; and $R^{8a}$ and $R^{8b}$ independently are: H, $C_1$-$C_4$alkyl, —$NO_2$, —$NR^4R^{22}$, —$OCH_3$, —$NR^4COOR^{22}$, —Cl, —$CH_2COOR^{4a}$, —$S(O)_x$—$R^{22}$, —$NR^4CONR^4R^{22}$, —$CH_2OCO(C_1$-$C_4$alkyl), —$NR^4COR^{22}$, —$CO_2R^{4a}$, —F, —$CH_2Ph$, or —$CONR^4R^{22}$.

6. A pharmaceutical formulation for the treatment of hypertension and congestive heart failure comprising a pharmaceutically acceptable carrier and an effective antihypertensive amount of the compound of claim 1.

7. An ophthalmological formulation for the treatment of ocular hypertension comprising an ophthalmologically acceptable carrier and an effective ocular antihypertensive amount of a compound of claim 1.

* * * * *